US012579645B2

(12) United States Patent
Sue et al.

(10) Patent No.: US 12,579,645 B2
(45) Date of Patent: Mar. 17, 2026

(54) SYSTEMS AND METHODS FOR PROCESSING IMAGES TO DETERMINE BIOMARKER LEVELS

(71) Applicant: PAIGE.AI, INC., New York, NY (US)

(72) Inventors: Jillian Sue, New York, NY (US); Marc Goldfinger, London (GB); Brandon Rothrock, Los Angeles, CA (US); Matthew Lee, London (GB)

(73) Assignee: Paige.AI, Inc., New York, NY (US)

( * ) Notice: Subject to any disclaimer, the term of this patent is extended or adjusted under 35 U.S.C. 154(b) by 281 days.

(21) Appl. No.: 18/451,507

(22) Filed: Aug. 17, 2023

(65) Prior Publication Data

US 2024/0062372 A1 Feb. 22, 2024

Related U.S. Application Data

(60) Provisional application No. 63/399,150, filed on Aug. 18, 2022.

(51) Int. Cl.
| | |
|---|---|
| *G06T 7/00* | (2017.01) |
| *G06T 5/50* | (2006.01) |
| *G06V 10/46* | (2022.01) |
| *G16H 30/20* | (2018.01) |
| *G16H 30/40* | (2018.01) |

(52) U.S. Cl.
CPC .............. *G06T 7/0012* (2013.01); *G06T 5/50* (2013.01); *G06V 10/462* (2022.01); *G16H 30/20* (2018.01); *G16H 30/40* (2018.01); *G06T 2207/20221* (2013.01); *G06T 2207/30024* (2013.01); *G06T 2207/30068* (2013.01)

(58) Field of Classification Search
CPC ..................... G06T 7/0012; G06T 5/50; G06T 2207/20221; G06T 2207/30024; G06T 2207/30068; G06T 2207/10056; G06T 2207/10081; G06T 2207/10088; G06T 2207/10104; G06T 2207/10116; G06T 2207/10132; G06T 2207/20084; G06T 2207/30096; G06V 10/462; G06V 10/764; G06V 10/82; G06V 2201/03; G16H 30/20; G16H 30/40; G16H 50/20; G06N 20/00
See application file for complete search history.

(56) References Cited

U.S. PATENT DOCUMENTS

| | | | | |
|---|---|---|---|---|
| 2020/0258223 A1* | 8/2020 | Yip | .......................... | G06F 18/21 |
| 2021/0071270 A1* | 3/2021 | Murillo | .................. | C12Q 1/686 |
| 2021/0073986 A1* | 3/2021 | Kapur | ....................... | G06T 7/11 |

(Continued)

*Primary Examiner* — Van D Huynh
(74) *Attorney, Agent, or Firm* — Bookoff McAndrews, PLLC

(57) ABSTRACT

Systems and methods are described herein for processing electronic medical images to predict a biomarker's presence, including receiving one or more digital medical images, the one or more digital medical images being of at least one pathology specimen associated with a patient. A machine learning system may determine a biomarker expression level prediction for the one or more digital medical images. The biomarker expression level prediction may be based on a determined transcriptomic score and protein expression score for the one or more digital medical images. A slide overlay indicating a region of tissue on the one or more digital medical images that is most likely to contribute to the slide level biomarker expression prediction may be generated.

19 Claims, 15 Drawing Sheets

700

(56)    References Cited

U.S. PATENT DOCUMENTS

| | | | |
|---|---|---|---|
| 2021/0166380 A1* | 6/2021 | Yip | G06N 3/045 |
| 2021/0350166 A1 | 11/2021 | Sue et al. | |
| 2022/0051047 A1* | 2/2022 | Kanan | G16H 50/20 |
| 2022/0189150 A1* | 6/2022 | Bentaieb | G06V 10/806 |
| 2025/0139765 A1* | 5/2025 | Kiemen | G06T 7/0012 |

* cited by examiner

200

300

350

400

450

500

550

552 — RECEIVE ONE OR MORE DIGITAL IMAGES OF A BREAST CANCER PATHOLOGY SPECIMEN

554 — DETERMINE, USING A MACHINE LEARNING SYSTEM, A BIOMARKER EXPRESSION LEVEL (E.G., A HER2 SCORE)

556 — SAVE AND OUTPUT DETERMINED BIOMARKER EXPRESSION LEVEL.

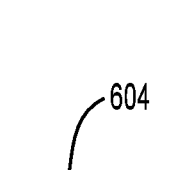
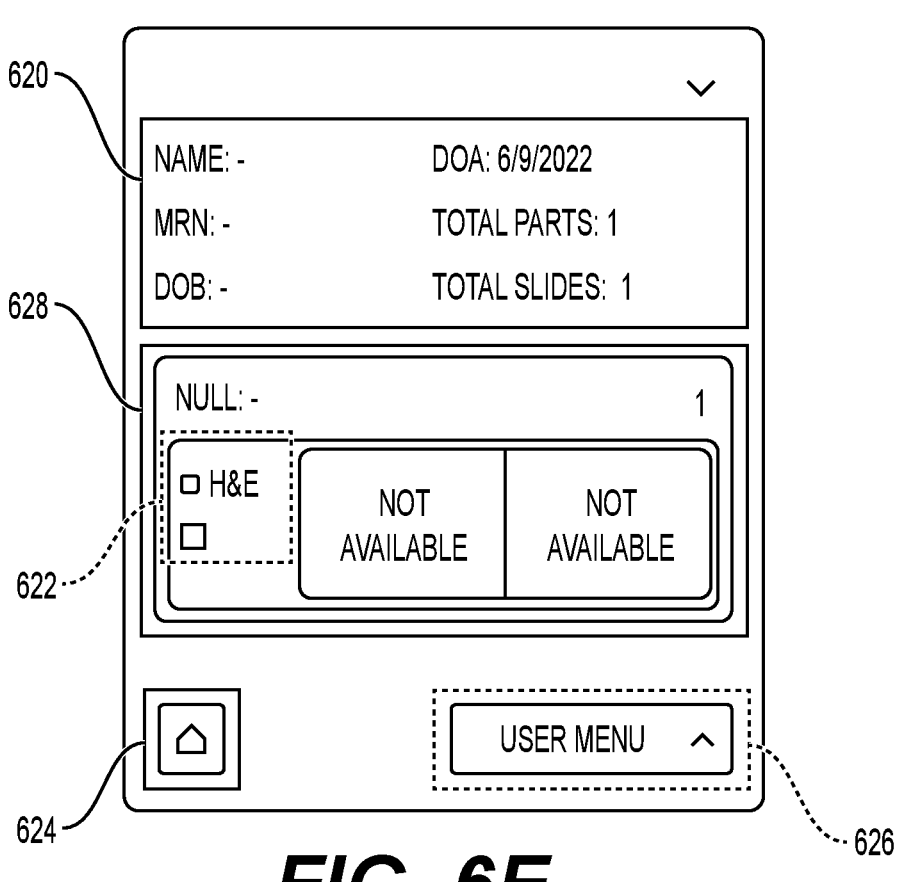
FIG. 6E

700

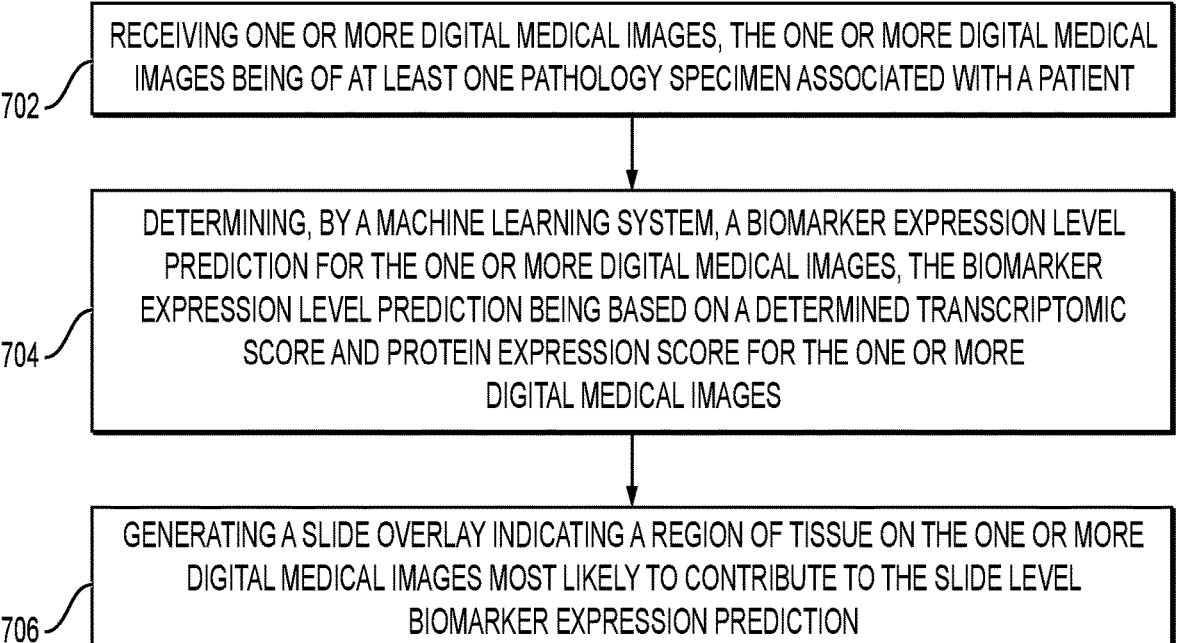

702  RECEIVING ONE OR MORE DIGITAL MEDICAL IMAGES, THE ONE OR MORE DIGITAL MEDICAL IMAGES BEING OF AT LEAST ONE PATHOLOGY SPECIMEN ASSOCIATED WITH A PATIENT

704  DETERMINING, BY A MACHINE LEARNING SYSTEM, A BIOMARKER EXPRESSION LEVEL PREDICTION FOR THE ONE OR MORE DIGITAL MEDICAL IMAGES, THE BIOMARKER EXPRESSION LEVEL PREDICTION BEING BASED ON A DETERMINED TRANSCRIPTOMIC SCORE AND PROTEIN EXPRESSION SCORE FOR THE ONE OR MORE DIGITAL MEDICAL IMAGES

706  GENERATING A SLIDE OVERLAY INDICATING A REGION OF TISSUE ON THE ONE OR MORE DIGITAL MEDICAL IMAGES MOST LIKELY TO CONTRIBUTE TO THE SLIDE LEVEL BIOMARKER EXPRESSION PREDICTION

*FIG. 7*

SYSTEMS AND METHODS FOR PROCESSING IMAGES TO DETERMINE BIOMARKER LEVELS

CROSS-REFERENCE TO RELATED APPLICATION(S)

This application claims the benefit of priority to U.S. Provisional Patent Application No. 63/399,150, filed Aug. 18, 2022, the entirety of which is incorporated by reference herein.

FIELD OF THE DISCLOSURE

Various embodiments of the present disclosure relate generally to image-based prediction of biomarkers and related image processing methods. More specifically, particular embodiments of the present disclosure relate to systems and methods for predicting one or more biomarkers levels based on processing images of tissue specimens.

BACKGROUND

Histological stains, such as Hematoxylin and Eosin (H&E), may be used in pathology to make cells visible. Many dye-based staining systems have been developed. However, the available dye-based systems and methods might not provide sufficient information for a pathologist to visually identify biomarkers that may aid diagnosis or guide treatment. In such instances, alternative techniques such as immunohistochemistry (IHC), immunofluorescence, in situ hybridization (ISH), and/or fluorescence in situ hybridization (FISH), may be used to identify a presence or absence of biomarkers. If these alternative techniques also fail to provide sufficient information (e.g., are inconclusive) for detecting biomarkers, genetic testing of the tissue may be used to confirm if a biomarker is present (e.g., overexpression of a specific protein or gene product in a tumor, amplification of a given gene in a cancer, etc.). However, genetic testing is costly and might not be available in many clinics and hospitals.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the present disclosure, systems and methods are disclosed for computer-implemented method for processing electronic medical images to predict a biomarker's presence, including: receiving one or more digital medical images, the one or more digital medical images being of at least one pathology specimen associated with a patient; determining, by a machine learning system, a biomarker expression level prediction for the one or more digital medical images, the biomarker expression level prediction being based on a determined transcriptomic score and protein expression score for the one or more digital medical images; and generating a slide overlay indicating a region of tissue on the one or more digital medical images most likely to contribute to the slide level biomarker expression prediction.

In some aspects, the techniques described herein relate to a method for determining, salient regions of the received one or more digital medical images prior to determining the biomarker expression level, wherein non-salient image regions are excluded from subsequent processing.

In some aspects, the techniques described herein relate to a method, wherein the one or more salient regions correspond to cancerous tissue.

In some aspects, the techniques described herein relate to a method, wherein the one or more digital medical images are images of breast tissue stained with hematoxylin and eosin.

In some aspects, the techniques described herein relate to a method, wherein the biomarker expression is human epidermal growth factor receptor 2.

In some aspects, the techniques described herein relate to a method, wherein the transcriptomic score is based on an immunohistochemistry (IHC) score for each of the one or more digital medical images.

In some aspects, the techniques described herein relate to a method, wherein the biomarker expression level prediction is performed upon determining that the received one or more slides has a immunohistochemistry (IHC) score of IHC-0 or IHC-1.

In some aspects, the techniques described herein relate to a method, wherein the protein expression score is based on an mRNA score for each of the one or more digital medical images.

In some aspects, the techniques described herein relate to a method, further including: determining a level of Erb-B2 Receptor Tyrosine Kinase 2 (ERBB2) mRNA, upon determining that an immunohistochemistry score is IHC-0+, indeterminate, or equivocal-IHC-1+.

In some aspects, the techniques described herein relate to a method, wherein the biomarker expression level prediction is determined to be a true absence of HER2 expression upon determining that the immunohistochemistry score is IHC-0+, indeterminate, or equivocal-IHC-1+ and that the ERBB2 mRNA score is less than 7.6.

In some aspects, the techniques described herein relate to a method, wherein generating a slide overlay includes generating a tissue map overlay and/or a heatmap overlay.

According to certain aspects of the present disclosure, a system is disclosed for processing electronic medical images, the system including: at least one memory storing instructions; and at least one processor configured to execute the instructions to perform operations including: receiving one or more digital medical images, the one or more digital medical images being of at least one pathology specimen associated with a patient; determining, by a machine learning system, a biomarker expression level prediction for the one or more digital medical images, the biomarker expression level prediction being based on a determined transcriptomic score and protein expression score for the one or more digital medical images; and generating a slide overlay indicating a region of tissue on the one or more digital medical images most likely to contribute to the slide level biomarker expression prediction.

In some aspects, the techniques described herein relate to a system, further including: determining, salient regions of the received one or more digital medical images prior to determining the biomarker expression level, wherein non-salient image regions are excluded from subsequent processing.

In some aspects, the techniques described herein relate to a system, wherein the one or more salient regions correspond to cancerous tissue.

In some aspects, the techniques described herein relate to a system, wherein the biomarker expression level prediction is performed upon determining that the received one or more slides has a immunohistochemistry (IHC) score of IHC-0 or IHC-1.

In some aspects, the techniques described herein relate to a system, wherein the protein expression score is based on an mRNA score for each of the one or more digital medical images.

In some aspects, the techniques described herein relate to a system, further including: determining a level of Erb-B2 Receptor Tyrosine Kinase 2 (ERBB2) mRNA, upon determining that an immunohistochemistry score is IHC-0+, indeterminate, or equivocal-IHC-1+.

In some aspects, the techniques described herein relate to a system, wherein the biomarker expression level prediction is determined to be a true absence of HER2 expression upon determining that the immunohistochemistry score is IHC-0+, indeterminate, or equivocal-IHC-1+ and that the ERBB2 mRNA score is less than 7.6.

According to certain aspects of the present disclosure, A non-transitory computer-readable medium is disclosed for storing instructions that, when executed by a processor, perform operations processing electronic medical images, the operations including: receiving one or more digital medical images, the one or more digital medical images being of at least one pathology specimen associated with a patient; determining, by a machine learning system, a biomarker expression level prediction for the one or more digital medical images, the biomarker expression level prediction being based on a determined transcriptomic score and protein expression score for the one or more digital medical images; and generating a slide overlay indicating a region of tissue on the one or more digital medical images most likely to contribute to the slide level biomarker expression prediction.

In some aspects, the techniques described herein relate to a non-transitory computer-readable medium, further including: determining a level of Erb-B2 Receptor Tyrosine Kinase 2 (ERBB2) mRNA, upon determining that an immunohistochemistry score is IHC-0+, indeterminate, or equivocal-IHC-1+.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 6E is a slide tray of the viewer, according to an exemplary embodiment of the present disclosure.

FIG. 7 illustrates an exemplary flowchart for processing images to determine a biomarker expression level, according to techniques presented herein.

DESCRIPTION OF THE EMBODIMENTS

Figure 1A:
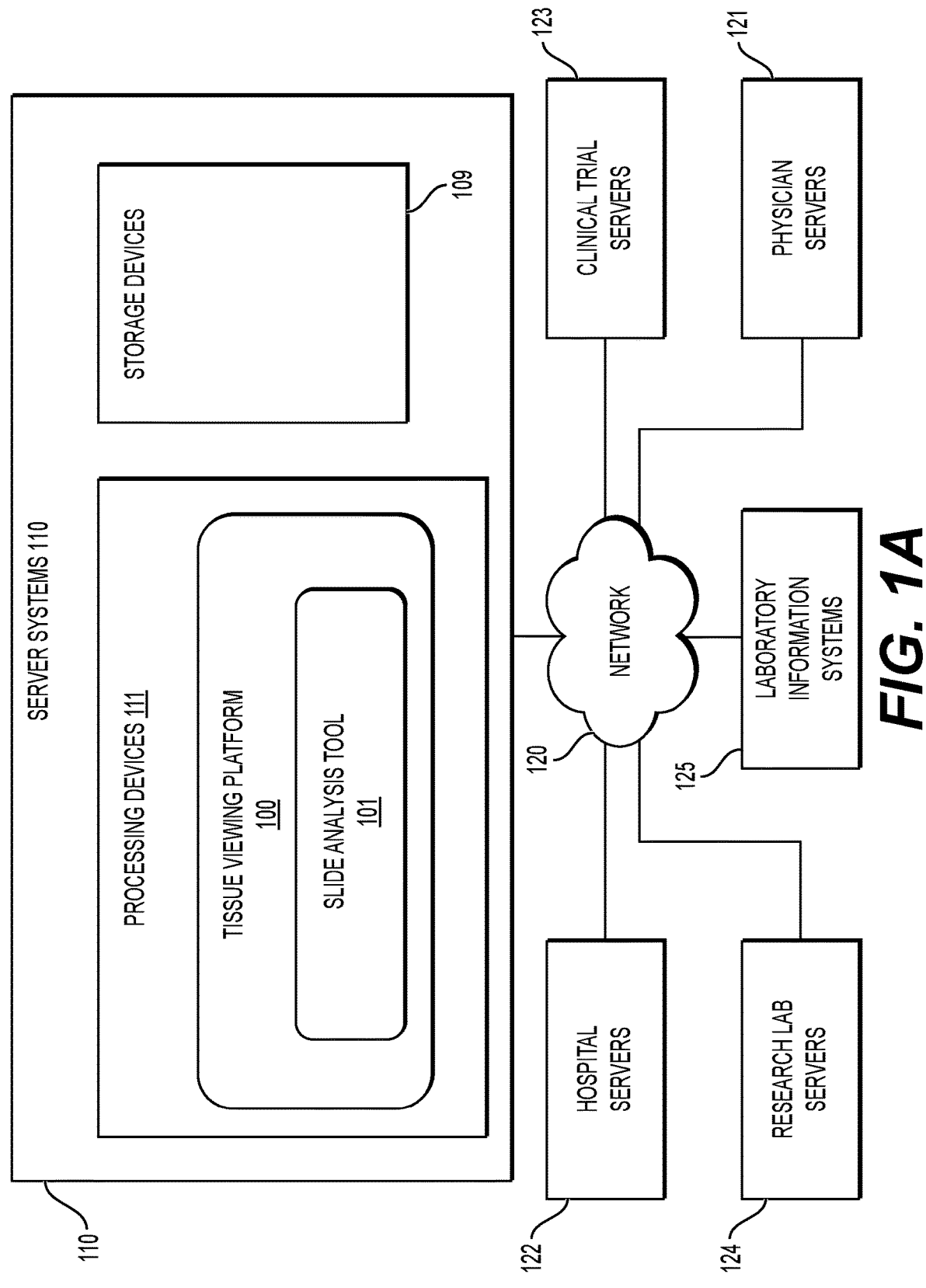
FIG. 1A illustrates an exemplary block diagram of a system and network for processing images to determine biomarker expression level, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the systems, devices, and methods described herein. None of the features or components shown in the drawings or discussed below should be taken as mandatory for any specific implementation of any of these systems, devices, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a"

and "an" herein do not denote a limitation of quantity, but rather denote the presence of one or more of the referenced items.

Systems and methods disclosed herein may describe a system and related methods for using artificial intelligence (AI) to predict biomarkers (e.g., the overexpression of a protein and/or gene product, amplification, and/or mutations of specific genes) from salient regions within digital images of tissues stained using H&E and/or other dye-based methods, and displaying the predictions in digital pathology viewing software. The systems and related methods disclosed herein may incorporate any of the features described in U.S. application Ser. No. 17/016,048, filed Sep. 9, 2020, the entirety of which is hereby incorporated by reference.

Systems and methods described herein may describe an artificial intelligence (AI")" digital assay capable of robustly and rapidly detecting biomarker activity of human epidermal growth factor receptor 2 ("HER2"), which may also be known as Erb-B2 Receptor Tyrosine Kinase 2 ("ERBB2"), from whole slide images ("WSI") of breast tissue stained, e.g., with hematoxylin and eosin ("H&E"). The system described herein may include a model trained using curated H&E WSI, with updated definitions of HER2 categories based on combining transcriptomic and protein expression methodologies. The model may define cases that are IHC-0 in addition to having no ERBB2 messenger ribonucleic acid ("mRNA") expression within the tissue as HER2-negative. This may effectively leverage two ground truths (e.g., IHC-0 as a first ground truth and no ERBB2 mRNA expression as a second ground truth) to determine a new true negative category. Additionally, the model may define cases that have an IHC score of IHC-1+/IHC-2+|ISH- and a mid-level expression of ERBB2 mRNA as HER2-expressing (also referred to as HER2-Low). The model may be able to identify HER2 expression in cases where IHC accurately classifies cases as negative due to faulty or poor IHC staining, or where the staining is equivocal (indeterminate IHC-0-1+) and are thus ineligible for next generation therapies (NGTs).

The model may detect morphological phenotypes consistent with HER2 expression. The categories of classification may include low levels of HER2 expression (HER2-Low), lack of or null HER2 expression (HER2-Negative), and normal or high levels of HER2 expression (HER2-amplified). This device may be intended to be used on breast H&E images of cases where the HER2 IHC has previously been determined to be IHC-0+, indeterminate or equivocal-IHC-1+. In another example, HER2 IHC may be determined alongside a HER2 expression level. The model may classify the sample as Low (HER2-Low) or Null (HER2-Negative). Additionally, the model may generate and provide tissue map and/or heatmaps for display to identify regions of the tissue that the model has identified as corresponding to (e.g., most likely contributing) the prediction.

The system described herein may predict a more advanced version of IHC score—whereby the system predicts a true absence of HER2 expression via IHC and mRNA (IHC-0 and mRNA<7.6), HER2 low expression (IHC-1+/IHC2+ and mRNA 9+) and HER2 Amplified (IHC3+/2+, potentially with a FISH testing examination for confirmation). mRNA may be used as a ground truth for HER2-negative. As mRNA is the precursor to protein expression, this may be used as a second mechanism to evaluate the "truth" of the IHC. IHC may be quite variable depending on the assay used, the reader, and/or the tissue quality, all of which may affect the IHC score. This may be particularly an issue at low levels of IHC, whereby the boundaries between IHC-0 and IHC-1 are blurred, and potentially not clinically meaningful. Effectively, the system may use the lack of mRNA as confirmation that the IHC-0 is a true HER2 negative (e.g., there is no protein expression because there is no mRNA to be translated). The true HER2 negative has a distinct phenotype from HER2-low in the H&E image. This allows the system to find cases that are IHC-0 but actually may express low levels of HER2 (e.g., cases that may have been misinterpreted or given an inaccurate score using conventional assays).

FIG. 1A illustrates an exemplary block diagram of a system and network for processing images to determine biomarker expression level, according to techniques presented herein.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices 111 that are configured to implement a tissue viewing platform 100, which includes a slide analysis tool 101 for determining specimen property or image property information pertaining to digital pathology image(s), and using machine learning to classify a specimen, according to an exemplary embodiment of the present disclosure. The tissue viewing platform 100 may also include histology breast biomarker tool 141 for determining a biomarker expression level. In other examples, the breast biomarker tool 141 may be operated separately from (e.g., by a different platform than) the tissue viewing platform 100.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125.

Figure 1B:
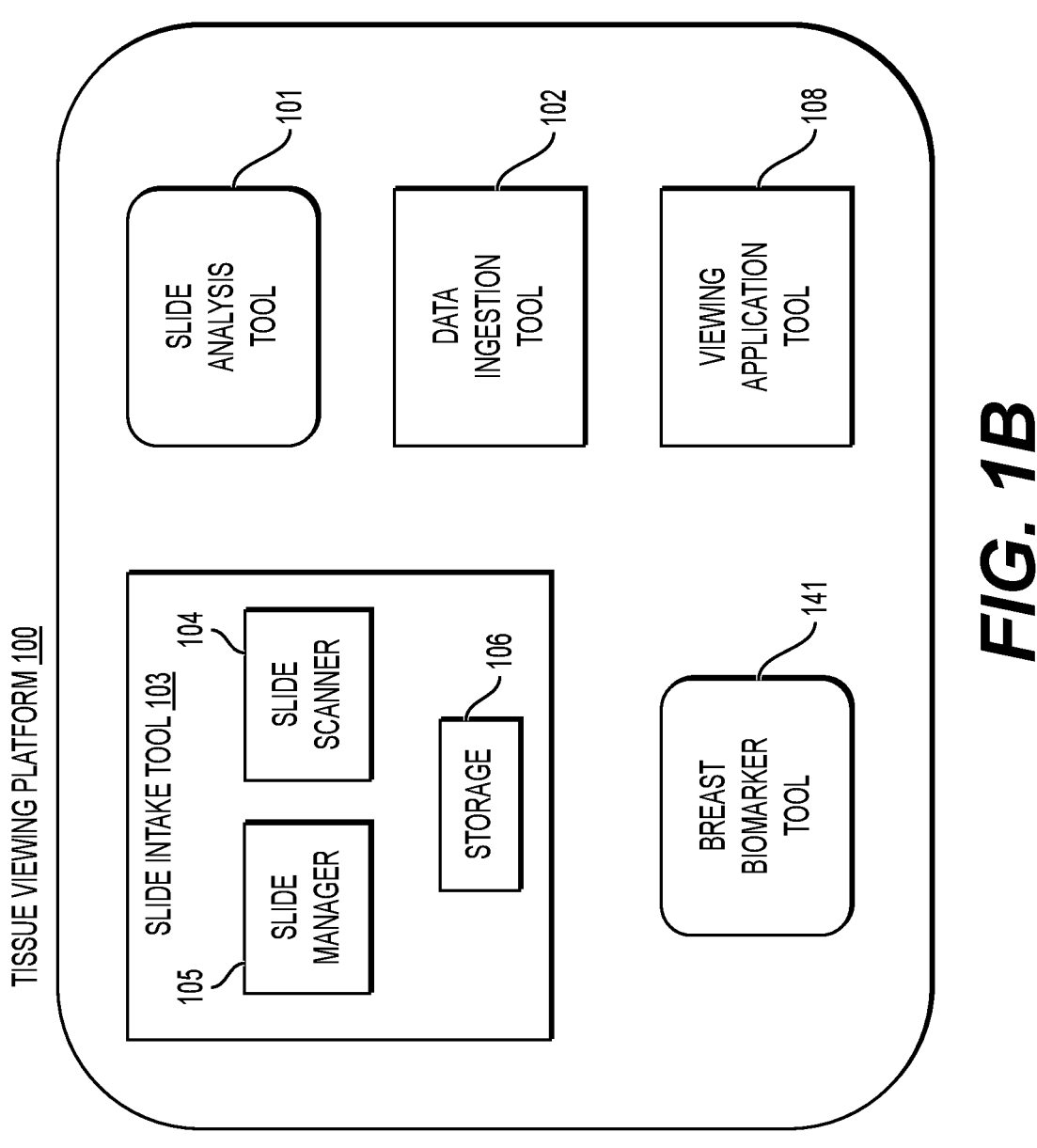
FIG. 1B illustrates an exemplary block diagram of a tissue viewing platform according to techniques presented herein.

FIG. 1B illustrates an exemplary block diagram of the tissue viewing platform 100. For example, the tissue viewing platform 100 may include a slide analysis tool 101, a breast biomarker tool 141, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen (e.g., digitized images of slide-mounted histology or cytology specimens), and using machine learning to analyze a slide, according to an exemplary embodiment.

The breast biomarker tool 141, as described in greater detail below, refers to a process and system for processing digital pathology slides (e.g., digitalized images of a slide-mounted history or cytology specimens), and using machine learning or a rules based system for determining a biomarker expression level. The biomarker expression level may include cell or tissue characteristics associated with a given disease, a grade, phase, stage, and/or severity associated with a disease, and/or the like. In an example, the biomarker expression level may refer to the human epidermal growth factor receptor 2 (HER2) expression level. In one example, the biomarker expression level may be based on both transcriptomic and protein expression methodologies.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.). For example, the viewing application tool 108 may connect to and/or include the systems described in FIG. 6A-6F.

The slide analysis tool 101 and breast biomarker tool 141, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the breast biomarker tool 141, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
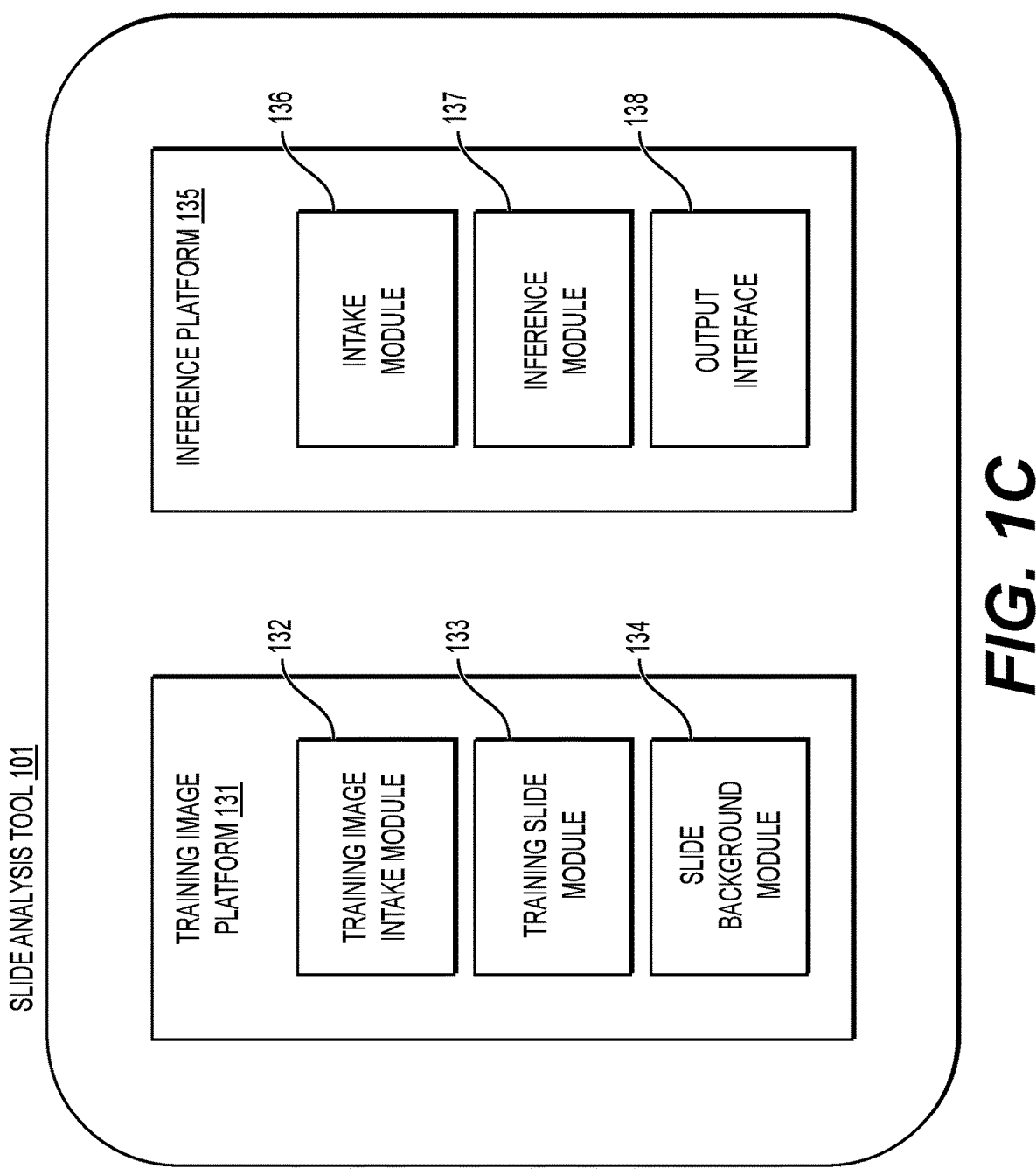
FIG. 1C illustrates an exemplary block diagram of a slide analysis tool, according to techniques presented herein.

FIG. 1C illustrates an exemplary block diagram of a slide analysis tool 101, according to an exemplary embodiment of the present disclosure. The slide analysis tool may include a training image platform 131 and/or an inference platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human and/or animal tissue and images that are graphically rendered. For example, the training images may be received from any one or any combination of the server systems 110, physician servers 121, and/or laboratory information systems 125. This dataset may be kept on a digital storage device. The training slide module 133 may intake training data that includes images and corresponding information. For example, training slide module 133 training data may include receiving one or more images (e.g., WSIs) of a human or animal. This dataset may be kept on a digital storage device. In some examples, the dataset may be comprised of a plurality of data subsets, where each data subset corresponds to a training case from a plurality of training cases and includes one or more training images from the training case. The training slide module 133 may include one or more computing devices capable of, e.g., determining whether the training images have a sufficient level-of-quality for training a machine learning model. The training slide module 133 may further include one or more computing devices capable of, e.g., identifying whether a set of individual cells belong to a cell of interest or a background of a digitized image.

The slide background module 134 may analyze images of tissues and determine a background within a digital pathology image. It is useful to identify a background within a digital pathology slide to ensure tissue segments are not overlooked.

According to one embodiment, the inference platform 135 may include an intake module 136, an inference module 137, and an output interface 138. The inference platform 135 may receive a plurality of electronic images/additional information and apply one or more machine learning model to the received plurality of electronic images/information to extract relevant information and integrate spatial and orientation information for display on medical digital images. For example, the plurality of electronic images or additional information may be received from any one or any combination of the server systems 110, physician servers 121, hospital servers 122, clinical trial servers 123, research lab servers 124, and/or laboratory information systems 125. The intake module 136 may receive WSI's corresponding to one or more patients/individuals. Further, the WSI's may correspond to an animal. The intake module 136 may further receive age, ethnicity, and ancillary test results and biomarkers such as genomic/epigenomic/transcriptomic/proteomic/microbiome information can also be ingested, e.g., point mutations, fusion events, copy number variations, microsatellite instabilities (MSI), or tumor mutation burden (TMB). The inference module 137 may apply one or more machine learning models to a group of WSI and any additional information in order to extract relevant information and integrate spatial and orientation information for display on medical images. The inference module 137 may further incorporate the spatial characteristics of the salient tissue into the prediction.

The output interface 138 may be used to output information about the inputted images and additional information (e.g., to a screen, monitor, storage device, web browser, etc.). Further, output interface 138 may output WSI's that indicate locations/salient regions that include evidence related to outputs from inference module 137.

Techniques discussed herein may use AI technology, machine learning, and/or image processing tools applied to determine a biomarker expression level. In some examples, both transcriptomic and protein expression methodologies may be utilized to determine a biomarker expression. In some examples, HER2 expression can be identified in cases where IHC inaccurately classifies a digital medical image where staining is poor or the results are equivocal (e.g., indeterminate IHC-0-1+).

In some aspects, the predictions as well as the analyzed images may be input to a visualization system that allows a user (e.g., a pathologist) to examine digital medical images, review corresponding biomarker expression levels, and generate a slide overlay indicating the focus on cancer most likely to contribute to the model's prediction. For example, as will be discussed in greater detail in FIG. 6A-6F, a user may be able to operate the visualization system/viewer via one or more panels to review the results (e.g., the biomarker expression levels) as well as the tissue of the digital medical images. Further, the visualization system may display a heat map that visualizes mutations and areas of interest. This may allow for a user to further inspect and review the digital medical images.

Figure 2:
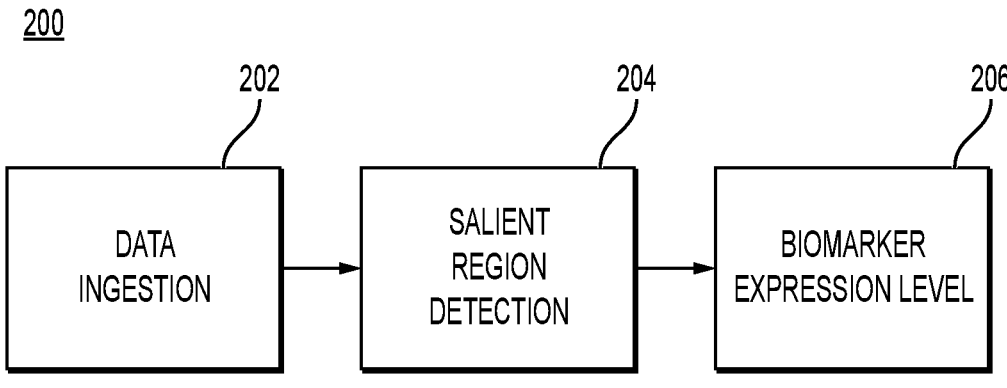
FIG. 2 illustrates an exemplary process for determining a biomarker expression level, according to techniques presented herein.

FIG. 2 illustrates an exemplary process 200 for a biomarker expression level determination, according to techniques presented herein. The systems and methods disclosed herein may include data ingestion 202, a salient region detection tool 204, and a biomarker expression level tool 206. The process described in FIG. 2 may be performed by the tissue view platform 100. In other examples, aspects of the system described in FIG. 2 may be performed in external systems and received by the tissue view platform 100. In one example, the salient region detection tool 204 may be performed by the slide analysis tool 101 and the biomarker expression level tool 206 may be performed by the breast biomarker tool 141.

In FIG. 2, the system may first include data ingestion 202. Data ingestion 202 may be performed by the slide analysis tool 101. Data ingestion may include receiving one or more digital images (e.g., whole slide image (WSI) of histopathological slide, cytology, magnetic resonance imaging (MRI), computed tomography (CT), positron emission tomography (PET), mammogram, ultrasound, X-rays, photographs of external anatomy, etc.) into a digital storage device 109 (e.g., hard drive, network drive, cloud storage, RAM, etc.). The one or more digital images may include one or more WSIs of histopathological slides prepared from tissue extracted during one or more biopsies and/or one or more resections of a given organ of a patient. Additionally or alternatively, digital images received may include images of the organ and/or region of the organ including an area of interest (e.g., an area having abnormal tissue and/or from which tissue is going to be or has been extracted as part of a biopsy or resection). In some examples, the digital images of the data ingested may be pre-processed. Data ingestion 202 may further include receiving metadata (e.g., from genetic testing, from IHC results analyzed by a pathologist, clinician annotations, etc.) about the biomarkers for each received image.

Next, data ingested may be inserted into a salient region detection tool 204 as described in greater detail below. A salient region detection tool 204, may be used to identify the salient regions to be analyzed for each digital image. This may be done manually by a human or automatically using AI/ML. An entire image or specific image regions can be considered salient. Salient region determination techniques are discussed in U.S. application Ser. No. 17/313,617, which is incorporated by reference herein in its entirety.

Exemplary methods may utilize the salient region detection tool 204 to identify tissue regions where cancer may be suspected. This may greatly reduce the sample complexity for the machine learning task, enabling biomarkers to be more efficiently learned by the biomarker expression level tool 206. For example, the salient region detection module may be configured to exclude non-salient region from subsequent processing by the biomarker expression level tool 206.

Next, the digital medical images from the data ingestion module 202, which may or not have had a salient region identified, may be provided to a biomarker expression level tool 206 (e.g., the breast biomarker tool 141). The biomarker expression level tool 206 may implement a trained machine learning system to predict the presence and/or level of a biomarker expression. For example, the biomarker expression level tool 206 may predict a HER2 expression level. The prediction may be output to an electronic storage device. A notification or visual indicator may be sent/displayed to a user, alerting the user to the presence or absence of one or more of the biomarkers.

The salient region detection tool 204 and the histology morphology prediction tool 206 are described further below.

The image region salient to biomarker detection, e.g., a tumor, may take a fraction of the entire image. Regions of interest can be specified by a human expert using an image segmentation mask, a bounding box, or a polygon. Alternatively, AI may provide a complete end-to-end solution in identifying the appropriate locations. Salient region identification may enable the downstream AI system to learn how to detect biomarkers from less annotated data and to make more accurate predictions.

One aspect of the systems and methods disclosed herein includes the automatic identification of one or more salient regions to be analyzed for a digital image using AI/ML. An entire image or specific image regions may be considered salient. The salient region may be assigned a continuous score of interest. The salient regions may correspond to areas of cancer and/or tissue mutations.

The continuous score of interest may be specific to certain structures within the digital image, and it can be important to identify relevant regions so that they can be included while excluding irrelevant ones. Salient region identification can enable the downstream machine learning system to learn how to detect histological morphologies from less annotated data and to make more accurate predictions.

As described in more detail below, with respect to the steps performed to train one or more machine learning systems to identify one or more salient regions of a digital image, there are multiple approaches to using machine learning to create a salient region detector. One approach includes strongly supervised methods that identify precisely where the histological morphology of interest could be found. Another approach includes weakly supervised methods that do not provide a precise location.

For strongly supervised training, the system may need the image and the location of the salient regions including the histological morphology of interest as input. For 2D images, e.g., WSIs, 2D ultrasound, X-rays, and photographs, these locations could be specified with pixel-level labeling, bounding box-based labeling, polygon-based labeling, or using a corresponding image where the saliency has been identified (e.g., using immunohistochemical (IHC) staining). For 3D images, e.g., CT and MRI scans, the locations could be specified with voxel-level labeling, using a cuboid, etc., or use a parameterized representation allowing for subvoxel-level labeling, such as parameterized curves or surfaces, or deformed template. For weakly supervised training, the system may require the image or images and the presence/absence of the salient regions, but the exact location of the salient location does not need to be specified.

The training of the salient region detection tool 204 may be described in greater detail below. Examples of training the salient region detection tool 204 may include method 300 of FIG. 3A. Examples of using the salient region detection tool 204 may include method 350 of FIG. 3B.

Figure 3A:
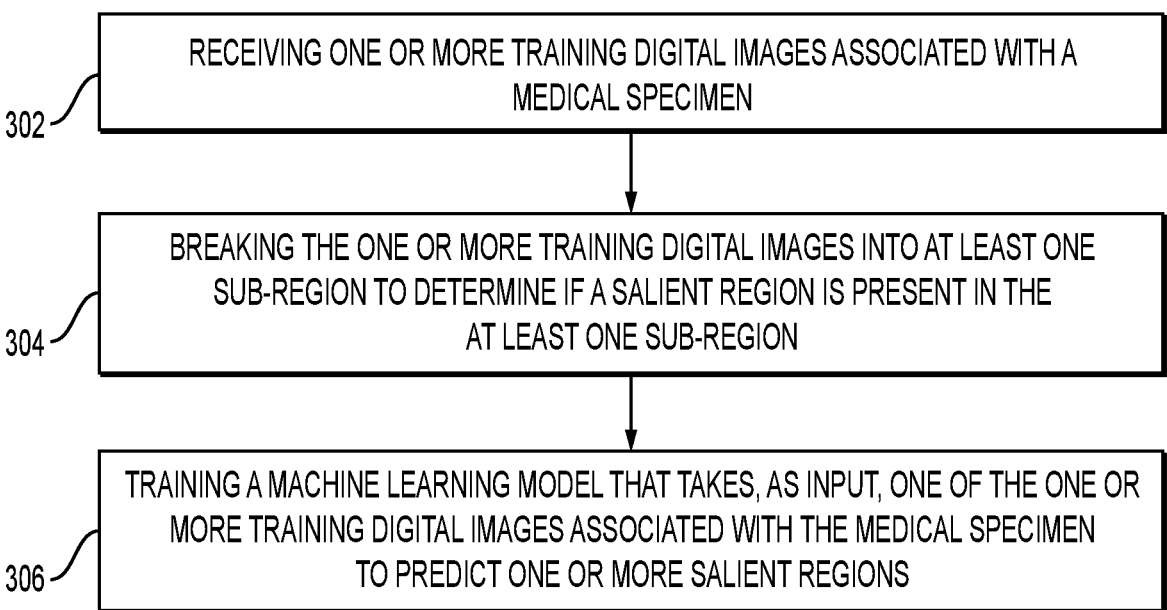
FIG. 3A is a flowchart illustrating an example method of training an algorithm for region detection, according to an exemplary embodiment of the present disclosure.

FIG. 3A is a flowchart illustrating an example method 300 of training an algorithm for region detection, according to an exemplary embodiment of the present disclosure. The method 300 of FIG. 3A depicts steps that may be performed by, for example, the slide analysis tool 101 as described above in FIG. 1C. Alternatively, the method may be performed by an external system. According to one example aspect, for training the one or more machine learning systems to identify one or more salient regions of a digital image, the following method 300 may be performed.

At step 302, the system may receive one or more digital images of a medical specimen (e.g., histopathological slide images, CT, MRI, PET, mammogram, ultrasound, X-rays, photographs of external anatomy, etc.) into a digital storage device (e.g., hard drive, network drive, cloud storage, RAM, etc.) and an indication of the presence or absence of the salient region (e.g., a particular organ, tissue, region of tissue, etc.) within the image.

At step 304, the system may, break each digital image into sub-regions that may then have their saliency determined. Regions can be specified in a variety of methods, including creating tiles of the image, segmentations based on edge/contrast, segmentations via color differences, segmentations based on energy minimization, supervised determination by the machine learning model, EdgeBoxes, etc.

At step 306 a machine learning system may be trained that takes as input a digital image and predicts whether the salient region is present or not. Training the salient region detection module may also include training a machine learning system to receive, as an input, a digital image and to predict whether the salient region is present or not. Many methods may be used to learn which regions are salient, including but not limited to weak supervision, bounding box or polygon-based supervision, or pixel-level or voxel-level labeling.

Weak supervision may involve training a machine learning model (e.g., multi-layer perceptron (MLP), convolutional neural network (CNN), transformers, graph neural network, support vector machine (SVM), random forest, etc.) using multiple instance learning (MIL). The MIL may use weak labeling of the digital image or a collection of images. The label may correspond to the presence or absence of a salient region. The label may correspond to the presence or absence of a salient region that could express the relevant biomarker.

Bounding box or polygon-based supervision may involve training a machine learning model (e.g., R-CNN, Faster R-CNN, Selective Search, etc.) using bounding boxes or polygons. The bounding boxes or polygons may specify sub-regions of the digital image that are salient for detection of the presence or absence of a biomarker, morphology, etc.

Pixel-level or voxel-level labeling (e.g., semantic or instance segmentation) may involve training a machine learning model (e.g., Mask R-CNN, U-Net, fully convolutional neural network, transformers, etc.) where individual pixels and/or voxels are identified as being salient for the detection of continuous score(s) of interest and/or biomarkers. Labels could include in situ tumor, invasive tumor, tumor stroma, fat, etc. Pixel-level/voxel-level labeling may be from a human annotator or may be from registered images that indicate saliency.

Using a corresponding, but different digital image that identifies salient tissue regions training may include receiving a digital image of tissue that highlights the salient region (e.g., cancer identified using IHC) and can be registered with the input digital image. For example, a digital image of an H&E image could be registered/aligned with an IHC image identifying salient tissue (e.g., cancerous tissue where the biomarker should be found), where the IHC can be used to determine the salient pixels based on image color characteristics.

According to another example aspect, to implement the one or more trained machine learning systems for identifying one or more salient regions in a digital image, the following steps may be performed, as described below.

Figure 3B:
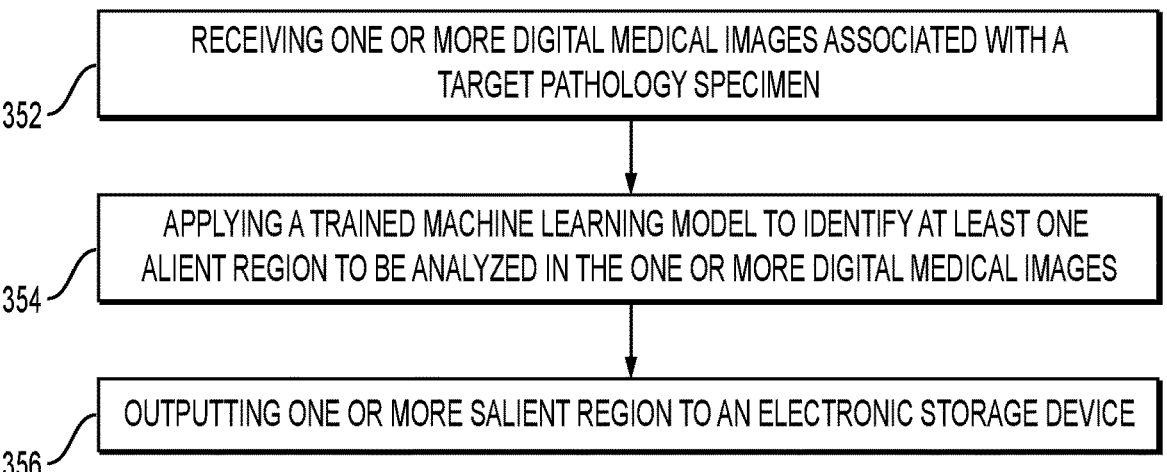
FIG. 3B is a flowchart illustrating an exemplary method of utilizing an algorithm for region detection, according to an exemplary embodiment of the present disclosure.

FIG. 3B is a flowchart illustrating methods for how to provide image region detection, according to one or more exemplary embodiments herein. FIG. 3B may illustrate a method that utilizes the neural network that was trained in FIG. 3A. The exemplary method 350 (e.g., steps 352-356) of FIG. 3B depicts steps that may be performed by, for example, by the slide analysis tool 101. These steps may be performed automatically or in response to a request from a user (e.g., physician, pathologist, etc.). Alternatively, the method described in flowchart 350 may be performed by any computer process system capable of receiving image inputs such as device 800 and capable of including or importing the neural network described in FIG. 3A.

At step 352, a system may receive one or more digital medical images may be received of a medical specimen into a digital storage device (e.g., hard drive, network drive, cloud storage, RAM, etc.). Using the salient region detection module may optionally include breaking or dividing each digital image into sub-regions and determining a saliency (e.g., sub-regions of tissue which has morphology of interest) of each sub-region using the same approach from training step 304. For example, regions can be specified by creating tiles of the image, segmentations based edge/contrast, segmentations via color differences, supervised determination by the machine learning model, EdgeBoxes, etc.

At step 354, the trained machine learning system from FIG. 3A may be applied to the inputted images to predict which regions of the image are salient and could potentially exhibit the continuous score(s) of interest. The salient regions and/or sub-regions may indicate cancerous tissue for which biomarker(s) may be identified.

At step 356, if salient regions are found at step 354, the system may identify the salient region locations and flag them. If salient regions are present, detection of the region can be done using a variety of methods, including but not restricted to: running the machine learning model on image sub-regions to generate the prediction for each sub-region; or using machine learning visualization tools to create a detailed heatmap, etc. Example techniques are described in U.S. application Ser. No. 17/016,048, filed Sep. 9, 2020, and Ser. No. 17/313,617, filed May 6, 2021, which are incorporated herein by reference in their entireties. The detailed heatmap may be created by using class activation maps, GradCAM, etc. Machine learning visualization tools may then be used to extract relevant regions and/or location information. Further, the non-salient images of the region may be excluded from subsequent processing and not sent to the biomarker expression level tool 206.

The outputted salient regions from step 356, may then be fed into the biomarker expression level tool 206. The training of biomarker expression level tool 206 may be described in greater detail below. Examples of training the biomarker expression level tool 206 may include method 400 of FIG. 4A and method 500 of FIG. 5A. Examples of using the biomarker expression level tool 206 may include method 450 of FIG. 4B and method 550 of FIG. 5B.

Figure 4A:
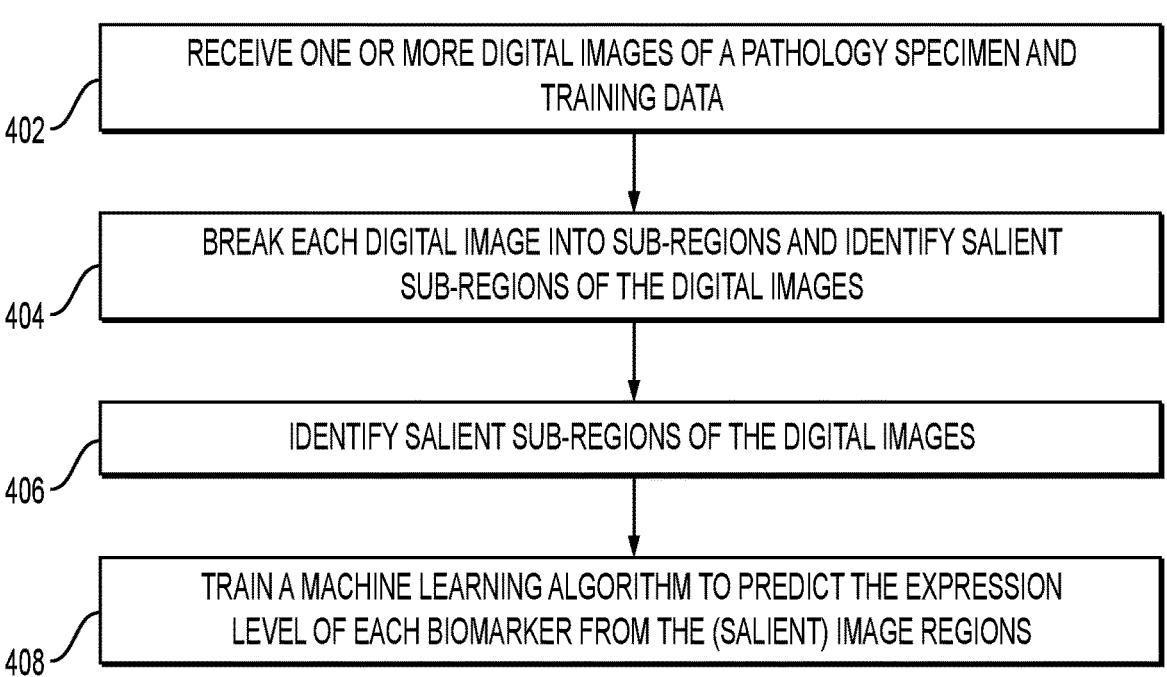
FIG. 4A is a flowchart illustrating an example method of training a biomarker expression level module according to an exemplary embodiment of the present disclosure.

FIG. 4A is a flowchart illustrating an example method 400 of training a biomarker expression level tool 206 according to an exemplary embodiment of the present disclosure. The method 400 of FIG. 4A depicts steps that may be performed by, for example, the biomarker expression level tool 206 as described above. Alternatively, the method 400, or certain steps thereof, may be performed by an external system.

At step 402, the system (e.g., the tissue viewing platform 100) may first receive training data. The training data may include one or more digital medical images with corresponding metadata. The one or more digital images of a pathology specimen may be (e.g., histology, cytology, etc.) The training data may be saved a digital storage device (e.g., hard drive, network drive, cloud storage, RAM, etc.). The received metadata corresponding to the digital medical images may include information, on the presence and/or the level of a biomarker present (e.g., binary or ordinal value) as well as the location of the biomarker. In some examples, the digital images may be annotated. In one example, the training data may include digital medical images of H&E breast biopsies and resection images.

At step 404, the system may break each of the received digital medical images into sub-regions. The system may perform this step utilizing any of the techniques described in FIG. 3A and FIB. 3B. For example, regions may be identified by a variety of methods, including creating tiles of the image, segmentations based edge/contrast, segmentations via color differences, supervised determination by the machine learning model, EdgeBoxes, etc. The training data may include metadata describing which of the sub-regions includes salient image regions. The salient regions may include regions of the digital medical image that correspond to a biomarker expression level prediction. For example, the salient regions may refer to cancerous tissue regions.

At step 406, the system may train a machine learning algorithm to predict the expression level of each biomarker from the (salient) image regions. Expression levels could be represented as binary numbers, ordinal numbers, real numbers, etc. This algorithm could be implemented in multiple ways, including but not limited to: Convolutional Neural Network ("CNN"), CNN trained with MIL, Recurrent neural network (RNN), Long-short term memory RNN (LSTM), Gated recurrent unit RNN (GRU), Graph convolutional network, Support vector machine, or Random Forrest. The machine learning system may further be trained to determine the area of the received slide that provides the support for the biomarker expression level. This location may be exported to the viewer 600 (described in FIG. 6A-6F below).

Figure 4B:
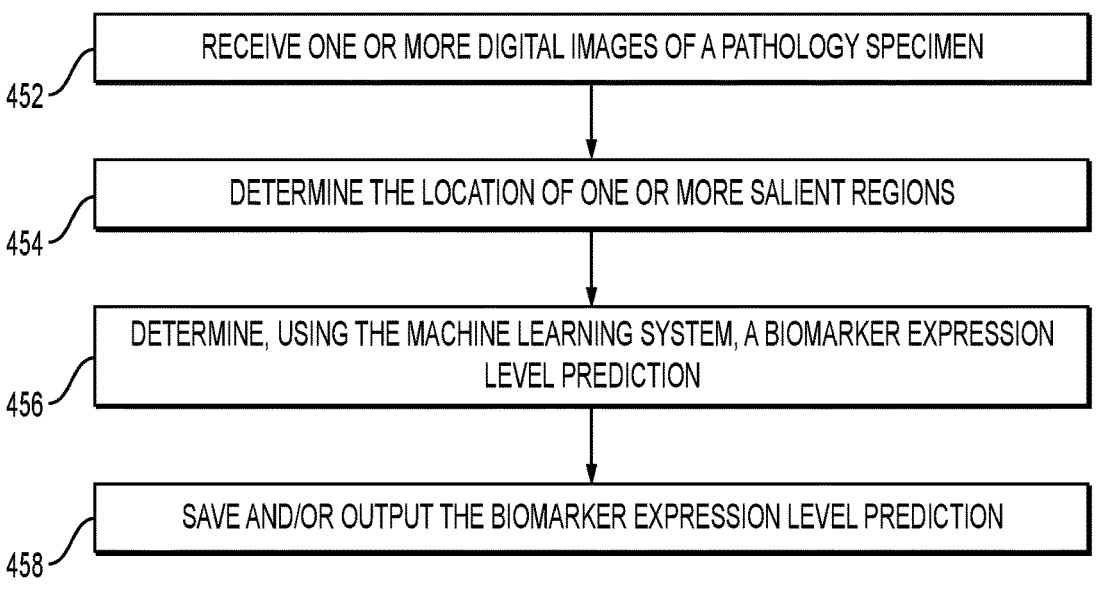
FIG. 4B is a flowchart illustrating an exemplary method of utilizing a biomarker expression level module according to an exemplary embodiment of the present disclosure.

FIG. 4B is a flowchart illustrating an exemplary method of utilizing a biomarker expression level tool 206 according to an exemplary embodiment of the present disclosure. The exemplary method 450 (e.g., steps 452-458) of FIG. 4B depicts steps that may be performed by, for example, the biomarker expression level tool 206. These steps may be performed automatically or in response to a request from a user (e.g., a pathologist, a department or laboratory manager, an administrator, etc.). Alternatively, the method 450 may be performed by any computer process system capable of receiving image inputs such as device 800 and capable of storing and executing the biomarker expression level tool 206.

At step 452, the system (e.g., the tissue viewing platform 100) may receive one or more digital images of a pathology specimen (e.g., histology, cytology, etc.) into a digital storage device (e.g., hard drive, network drive, cloud storage, RAM, etc.).

At step 454, the system may determine the location of one or more salient regions. In one example, the system may receive the salient regions as input at step 452. For example, the salient regions may have been determined externally of the system and inserted with the digital medical images at step 452. In one example, the slides may have been manually annotated by an expert. In another example, the salient region detection tool 204 may determine the salient regions.

At step 456, the system may apply the trained machine learning system (described in FIG. 4A) of the biomarker expression level tool 206 to the received images or the salient regions of the received images. The trained machine learning system may determine and output a prediction of whether the biomarker is present.

Last, at step 458, the system may output the prediction to a user and to an electronic storage device. For example, the prediction may be output the viewer 600 described in FIG. 6A-6F. The output may display a visual indicator to alert the user (e.g., a pathologist, histology technician, etc.) to the presence of the biomarker.

Figure 5A:
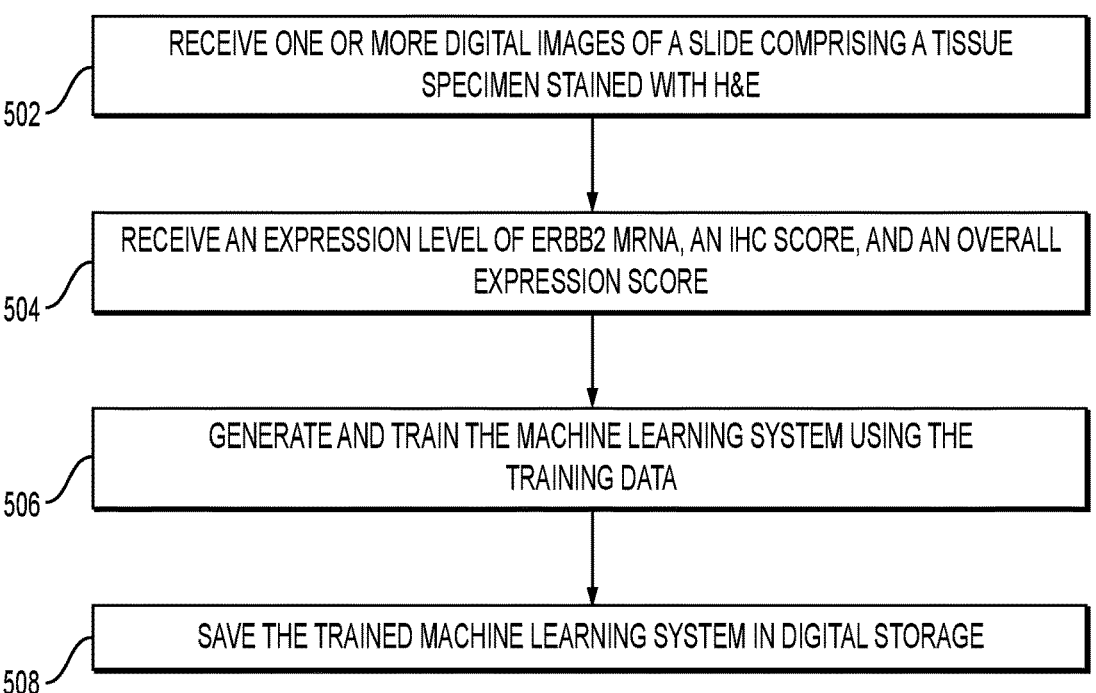
FIG. 5A is a flowchart illustrating an example method of training a biomarker prediction tool for determining a biomarker activity expression of human epidermal growth factor receptor 2 ("HER2"), according to an exemplary embodiment of the present disclosure.

FIG. 5A is a flowchart illustrating an example method of training a biomarker expression level tool 206 for determining a HER2 expression level according to an exemplary embodiment of the present disclosure. The method 500 of FIG. 5A depicts steps that may be performed by, for example, the biomarker expression level tool 206 as described above. Alternatively, the method 500, or certain steps thereof, may be performed by an external system.

First, at step 502, the system (e.g., the tissue viewing platform 100) may receive one or more digital images of a slide comprising a tissue specimen stained with H&E into a digital storage device (e.g., hard drive, network drive, cloud storage, RAM, etc.). The images may include mammaprints. In one example, the system may receive more than 1,200-curated H&E WSIs.

At step 504, the system may receive and store, for each of the received digital medical images from step 502, a corresponding IHC score (e.g., a protein expression score) and an ERBB2 mRNA score (e.g., a transcriptomic score). The system may further receive an overall expression score corresponding to each received digital medical image. The overall expression score may be either: (1) "true absence of HER2 expression," (2) "low expression," or "amplified expression." The true absence of HER2 expression score may correspond to a digital image with the following scores IHC-0 and mRNA<7.6, where the mRNA score may be derived by genetic sequencing of the original tissue sample. The HER2 low expression score may correspond to a digital image with the following scores IHC-1+/IHC2+ and mRNA 9+. The HER2 Amplified score may correspond to a digital image with the following scores IHC3+/2+ that may include a FISH test confirmation.

As discussed above, the system may receive a protein expression (e.g., an IHC score) corresponding to each of the received digital medical images of step 502. The level of expression can be on a numeric, ordinal, or binary scale. The protein expression score may be graded using IHC on a scale of 0, 1+, 1+ to 2+, 2+, and/or 3+, also referred to herein as an IHC score. The indication can be assigned to the entire image or image subregions, e.g., the image can be split into tiles and each tile could be assigned the HER2 expression level. The indication may include categorical data, e.g., "low risk" or "high risk." For example, an indication may comprise results of Oncotype DX.

The system may receive an expression level of ERBB2 mRNA corresponding to each of the received digital medical images of step 502. The ERBB2 mRNA score may be graded on a numeric scale (e.g., from 0 to 100.

Next, the system may identify salient image regions of each received image from step 502. The salient region may correspond to cancerous tissue. The salient region may be determined using either an AI-based method (e.g., the salient region detection tool 204) or by manual specification.

Last, at step 506, the system may train a machine learning system (e.g., the biomarker expression level tool 206) that learns how to predict the level of the biomarker present, based on the (salient) regions of the digital image of the pathology specimen, the received biomarker/score information, and/or the received expression level of ERBB2 mRNA. The machine learning system may be trained to identify and score an ERBB2 mRNA score and/or to identify an IHC score. In one example, the machine learning system may be trained to receive an IHC score and only determine a ERBB2 mRNA score. Both the ERBB2 mRNA score and/or IHC score may be determined for the whole digital image or be determined for a plurality of sub-regions/tiles of the digital medical images. In particular, the system may examine the expressed level of ERBB2 mRNA when the IHC score indicates a score of IHC-0 or IHC-1. The system may be trained to analyze the level of ERBB2 mRNA for these particular scores and, when no ERBB2 mRNA is present, the system may indicate a true IHC-0 negative score. The model may define cases that are IHC-0 in addition to having no ERBB2 mRNA expression within the tissue as HER2-negative. This may effectively leverage two ground truths (e.g., IHC-0 as a first ground truth and no ERBB2 mRNA expression as a second ground truth) to determine a new true negative category (i.e., the "true absence of HER2 expression score). Additionally, the model may define cases that have an IHC score of IHC-1+/IHC-2+lISH- and a mid-level expression of ERBB2 mRNA as HER2-expressing (also referred to as HER2-Low). The model may be able to identify HER2 expression in cases where IHC accurately classifies cases as negative due to faulty or poor IHC staining, or where the staining is equivocal (indeterminate IHC-0-1+) and are thus ineligible for next generation therapies (NGTs). In one example, when the machine learning system is trained to predict both an ERBB2 mRNA score and an IHC score, the trained machine learning system may further aggregate both the ERBB2 mRNA score and an IHC score to an aggregate score for output that synthesizes both scores.

The training method may be implemented in multiple ways. For example, according to one embodiment, the algorithm may be implemented by any one or any combination of (1) machine learning algorithms and/or architectures, such as neural network methods, e.g., convolutional neural networks (CNNs), vision transformers (ViT) and recurrent neural networks (RNNs); (2) training methodologies, such as Multiple Instance Learning, Reinforcement Learning, Active Learning, etc.; (3) long-short term memory RNN (LSTM); (4) gated recurrent unit RNN (GRU); (5) Graph convolutional network; (6) support vector machine; and/or (7) random forest. In one example, the algorithm may preferably be trained with more than one of the training methods listed above.

Additionally, the model may be trained to generate and provide tissue map and/or heatmaps for display to identify regions of the tissue that the model has identified as corresponding to (e.g., most likely contributing) the prediction.

At step 508, the trained machine learning system may be saved in digital storage.

In one example, the system may be trained on a mixture of breast biopsy and breast resection H&E images that are annotated by pathologists (e.g., the images have corresponding classification labels). According to techniques presented herein, three categories (e.g., types of labeled images) used for training and exemplary corresponding image numbers include:

(1) HER2-Negative: H&E images derived from cases whereby the IHC-0 and ERBB2 mRNA is absent: 116 WSIs (2) HER2-Expressing (HER2-Low): H&E images derived from cases whereby the IHC was IHC-1 and IHC-2, with FISH-negative: 930 WSIs (3) HER2-Amplified: H&E images derived from cases whereby the IHC-2+ and FISH-positive and IHC-3+ and genetically amplified ERBB2 expression as identified by IMPACT: 181 WSIs In one example, the model may be trained using a 10-fold cross validation method, employing a 8:1:1, train tune and test method.

The system may be validated on a held-out test set of 42 samples with corresponding whole slide images of breast biopsies and resection slides stained with hematoxylin and eosin (H&E) that are digitized using a scanner, such as a Leica AT2 scanner. As one example, the set of 42 samples may be comprised of 6 HER2 Null cases and 36 HER2 Low cases. In some examples, each of the samples may be from patient cases prepared, reviewed, diagnosed and digitized at a single institution. In other examples, the samples may come from a variety of different institutions or facilities. Additionally, in some examples, each sample may have come from a unique patient.

Further, in some examples, slides used to train the system may not be used to test and/or otherwise validate the system.

Additionally, slides used to test and/or otherwise validate the system may not overlap between biomarkers.

In one exemplary testing of the trained model using the parameters (e.g., the categories and corresponding image numbers described above), the BBM-HER2 group-level classification sensitivity (defined as correctly identifying true HER2 Null cases) was 33.33%, and specificity (defined as correctly identifying true HER2-Expressed cases) was 100%, with a PPV: 100%, NPV: 90% and overall Accuracy: 90.48%.

Figure 5B:
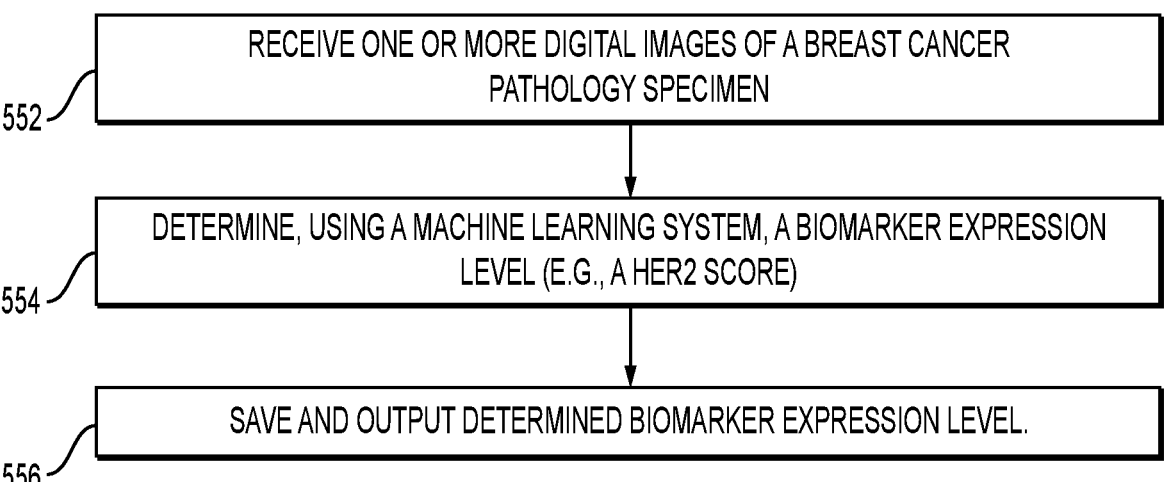
FIG. 5B is a flowchart illustrating an exemplary method of utilizing a biomarker prediction tool use for determining a HER2 expression level according to an exemplary embodiment of the present disclosure.

FIG. 5B is a flowchart illustrating an exemplary method of utilizing a biomarker prediction module use for HER2 low and mRNA according to an exemplary embodiment of the present disclosure. The exemplary method 550 (e.g., steps 552-556) of FIG. 5B depicts steps that may be performed by, for example, the biomarker expression level tool 206. These steps may be performed automatically or in response to a request from a user (e.g., a pathologist, a department or laboratory manager, an administrator, etc.). Alternatively, the method 550 may be performed by any computer process system capable of receiving image inputs such as device 800 and capable of storing and executing the biomarker expression level tool 206.

First, at step 552, the system (e.g., the tissue viewing platform 100) may receive one or more digital images of a breast cancer pathology specimen into a digital storage device (e.g., hard drive, network drive, cloud storage, RAM, etc.). The digital images of breast tissue may be stained, e.g., with hematoxylin and eosin ("H&E").

Next, the system may identify salient image regions that correspond to cancerous tissue using either an AI-based method (e.g., using the Salient Region Detection tool 204) or by manual specification.

Next, at step 554, the system may apply the machine learning biomarker detection system (e.g., the biomarker expression level tool 206) to the image to determine and output a prediction of each biomarker's expression level. The trained system may determine an IHC score and/or a ERBB2 mRNA score corresponding to each of the received digital images.

The system may group expression levels into diagnostic categories. For example, HER2 may be graded using IHC on a scale of 0, 1+, 1+ to 2+, 2+, and 3+. Using a probabilistic ordinal regression model, the probability of various combinations may be computed, e.g., the probability that the score is greater than zero may be computed. This may be important as suggested treatment such as drugs determined based on the score may only effective, depending on the level of expression. When an IHC score of 0 or 1+ is determined, the system may then examine the ERBB2 mRNA score amount to determine whether a true HER2 negative score is present. The model may classify the sample as Null (HER2-Negative) or Low (HER2-Low) based on IHC and mRNA (IHC-0 and mRNA<7.6), HER2 low expression (IHC-1+/IHC2+ and mRNA 9+) respectively, where the mRNA score may be specific to the Oncotype Dx panel Next, at step 556, the system may save and output the prediction to an electronic storage device. Outputting the prediction may include outputting the digital medical image with a visual indicator to alert the user (e.g., a pathologist, histology technician, etc.) of the expression levels of each biomarker. FIG. 6A-6F, as will be described in greater detail below, depict various outputs and interfaces that the system may include for the biomarker expression level.

Last, the system may recommend treatments that are potentially effective for the cancer given the biomarkers present.

The system described herein may be referred to as Breast Biomarker "BBM." BBM may be an in vitro diagnostic medical device software, derived from a deterministic deep learning model that has been trained with digitized H&E stained breast biopsies and resection slides that have been previously diagnosed. The BBM may for example include the tissue viewing platform 100. The BBM may detect the presence or absence of BBM mutations and expressions (HER2-expression and HER2 negative) within breast carcinomas for digitized H&E breast biopsy and resection images.

For each analyzed slide, the system may: (1) identify the slide level presence (Low; HER2-Low) or absence (Null; Her2-Negative) of HER2-expression using the trained model (as described in FIG. 4B and FIG. 5B), and detail this within the workflow; and (2) the BBM generates a slide overlay indicating the region of tissue (e.g., a focus of cancerous tissue) most likely to contribute to the model's prediction.

Figure 6A:
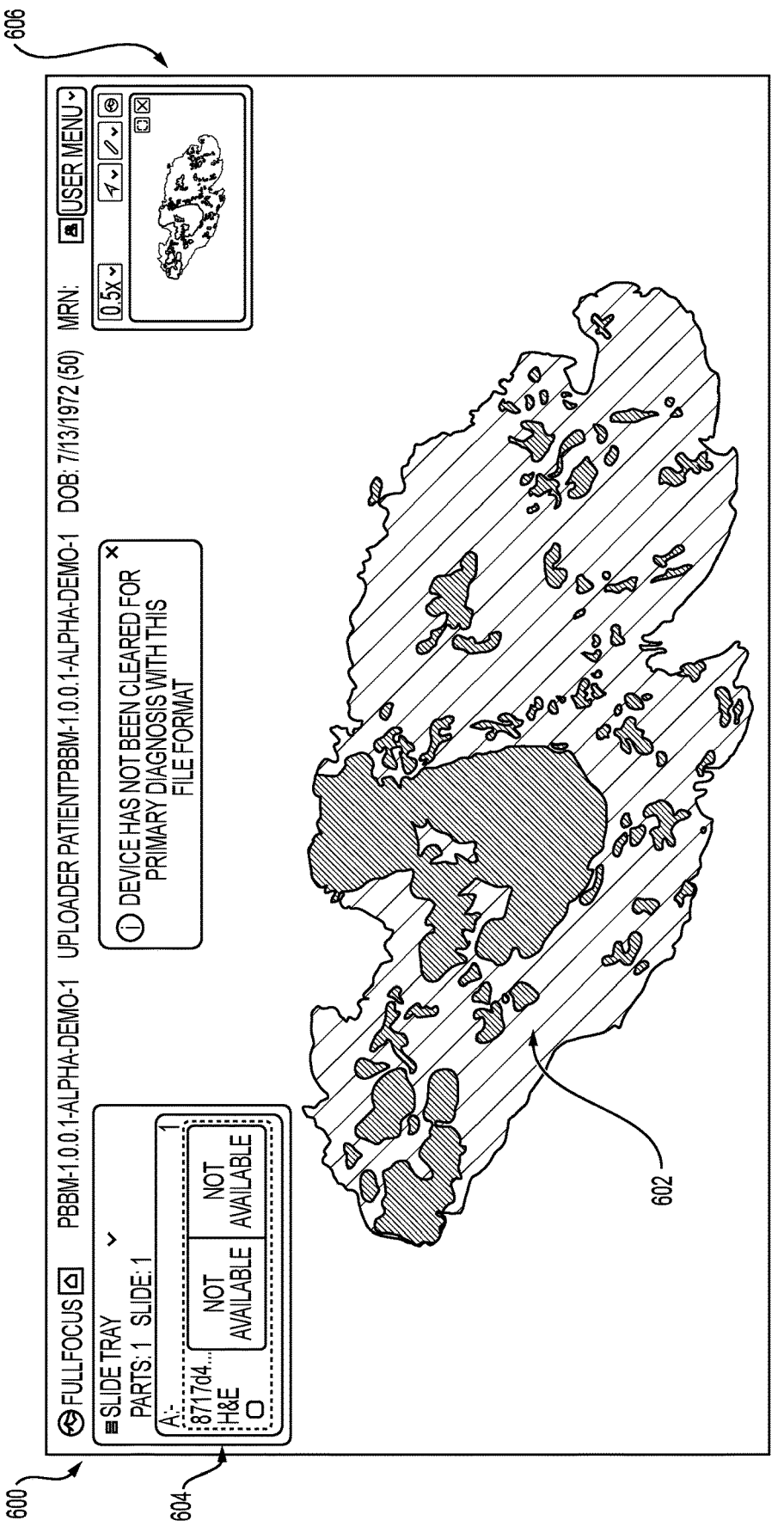
FIG. 6A is a vitro diagnostic medical device software viewer, according to an exemplary embodiment of the present disclosure.

FIG. 6A is a vitro diagnostic medical device software viewer 600, according to an exemplary embodiment of the present disclosure. The viewer 600 may be accessed by for example the viewing application tool 108 of the tissue viewing platform 100.

The BBM may be intended for use with digitized breast biopsy and resection H&E images. These images may be generated with a digital pathology scanning device.

A user (e.g., a pathologist) may ensure that the image is free of scanning artifacts, non-H&E staining, non-breast tissue as these may affect the accuracy of the device.

The BBM may include a viewer 600 that displays the WSI depicting breast tissue 602. The viewer 600 may include a slide tray 604 and a work panel 606. In some examples, personal health information (PHI) may be displayed within the slide tray. In other examples, if based on local rules or regulations of a geographical region in which the system is being executed, PHI display is restricted or otherwise unavailable, the PHI may not be included within the slide tray.

To control the viewer 600, the user may do so via the work panel 606 on the right-hand side of the screen To display the results of the breast biomarker (BBM) panel (HER2 null v low), the user may simply click the 'display AI' button 608 at the top right (e.g., the Logo). The user may change the magnification and detail while using the system. This may be done on the viewer tool by focusing on sections of the image through an image magnification button 610 and an image viewer 611 respectively.

Figure 6B:
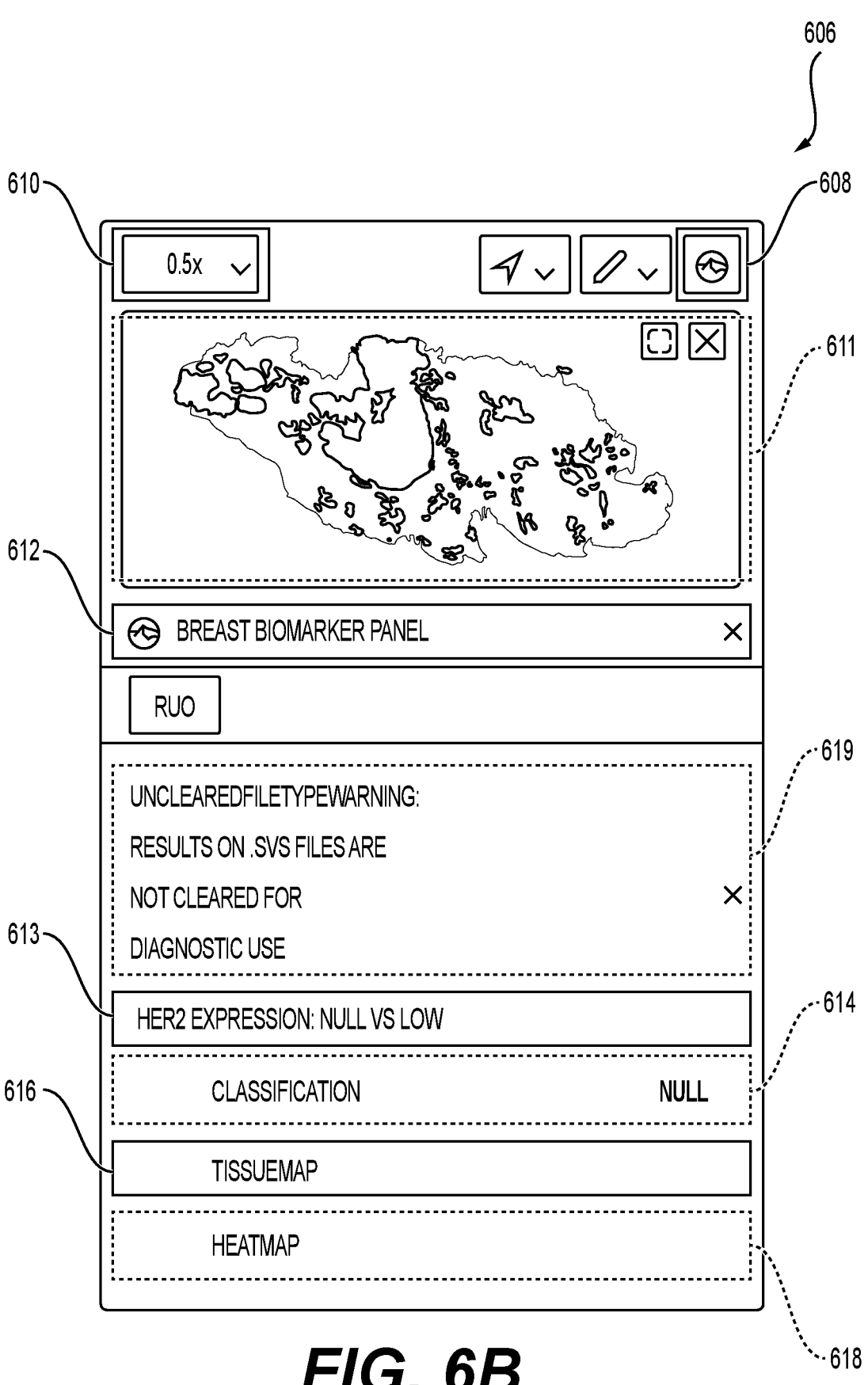
FIG. 6B is a work panel of the viewer, according to an exemplary embodiment of the present disclosure.

FIG. 6B is a work panel of viewer 600, according to an exemplary embodiment of the present disclosure. The work panel 606 may also include the name 612 of the algorithm applied by the viewer 600. The work panel 606 may further include the specific biomarker 613 searched for, a biomarker result 614, a button to display a tissue map overlap 616, and a button to display a heatmap overlay 618. A biomarker result 614 prediction of Null (HER2-negative) may indicate that the slide does not contain signals associated with HER2 expression. If the sample contains signals associated with lower HER2 expression, the prediction may be Low (HER2-Low). Users may be able to choose to visualize where in the WSI the model has identified the signals contributing to the prediction with one or more viewing options, such as a heatmap overlay 618 and/or a tissue map overlay 616. For example, the heatmap overlay 618 may visualize the mutation, where darker colors and red may indicate an increased likelihood of signal veracity, and lighter colors leading to blue may indicate a decreased likelihood. As another example, the tissue map overlay 616 may highlight the area of interest, making the region easy to detect and inspect further, as displayed in FIG. 6D. The work panel 606 may further include a file type warning 619 that indicates what type of file was inputted into the BBM.

Figure 6C:
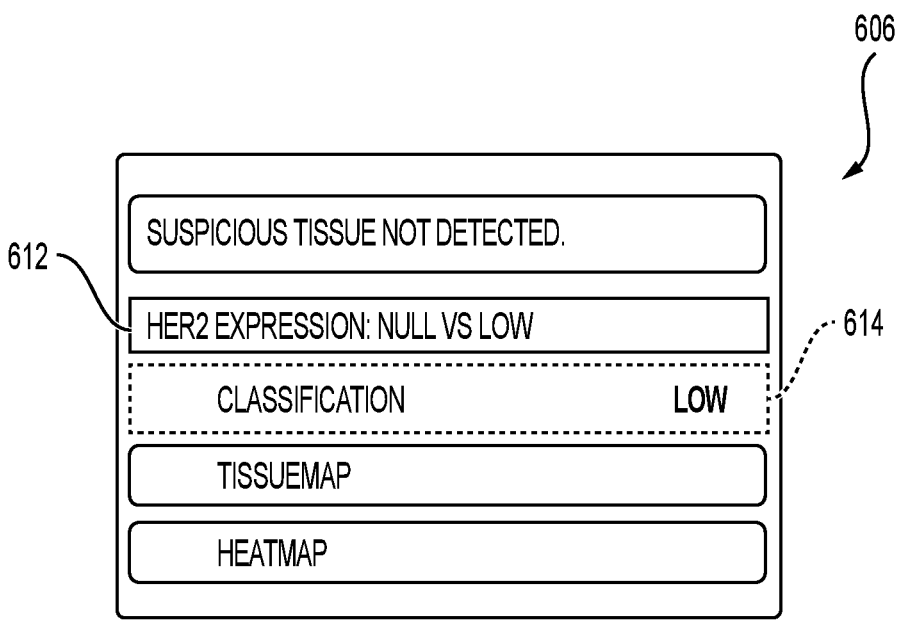
FIG. 6C is a work panel of the viewer indicating HER2-expression, according to an exemplary embodiment of the present disclosure.

FIG. 6C is a work panel 606 of the viewer indicating HER2-expression, according to an exemplary embodiment of the present disclosure. For example, the result 614 of the exemplary viewer 600 in FIG. 6C is Low (HER2-Low).

Figure 6D:
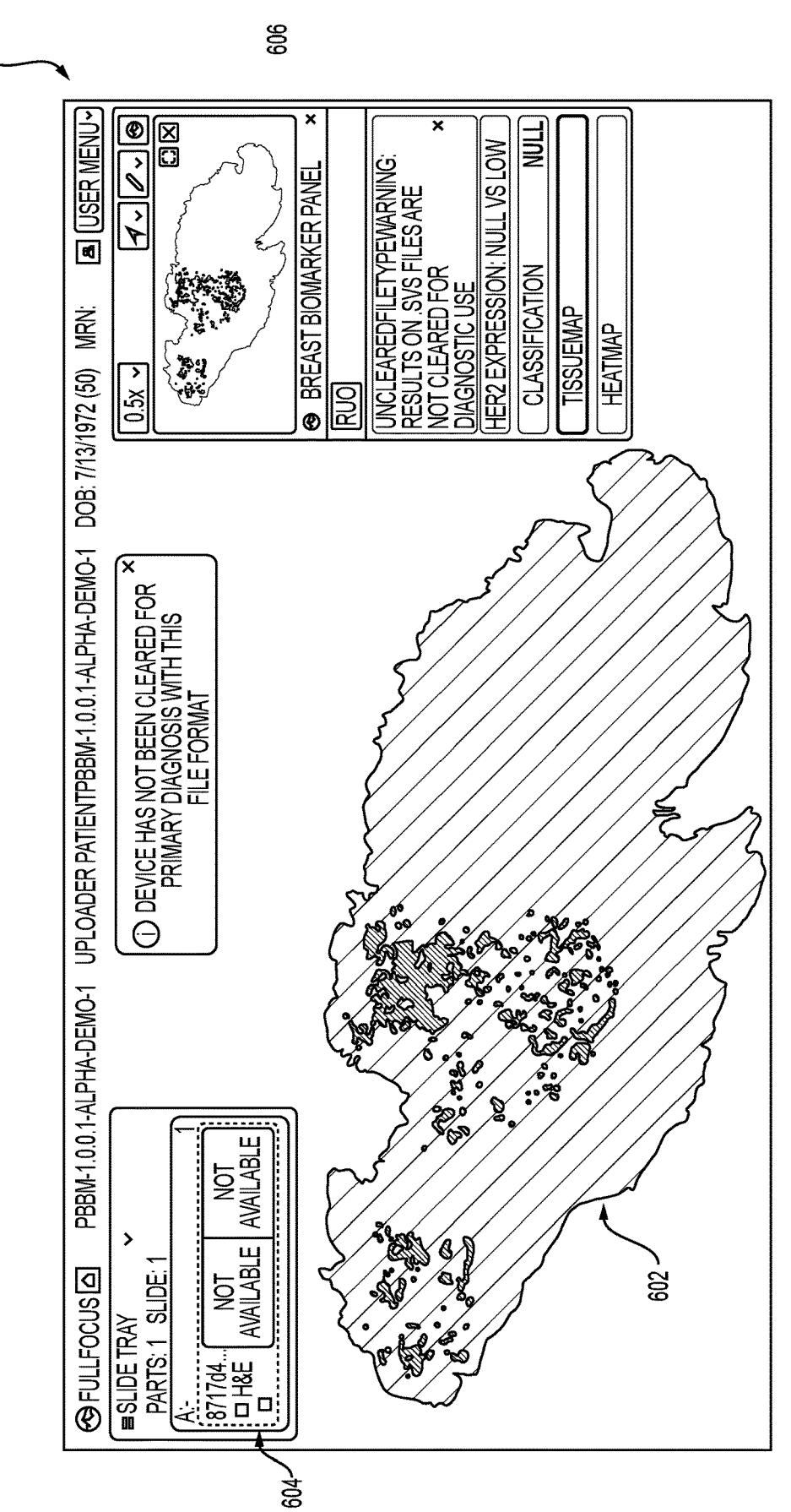
FIG. 6D is a vitro diagnostic medical device software viewer displaying the tissue map overlay of the location of HER2-negative, according to an exemplary embodiment of the present disclosure.

FIG. 6D is a vitro diagnostic medical device software viewer 600 displaying the tissue map overlay of the location of HER2-negative, according to an exemplary embodiment of the present disclosure. For example, the tissue map overlay 616 is toggled on in viewer 600 of FIG. 6D. The viewer 600 may depict the location of HER2-negative (null) phenotype identified by the BBM.

Figure 6F:
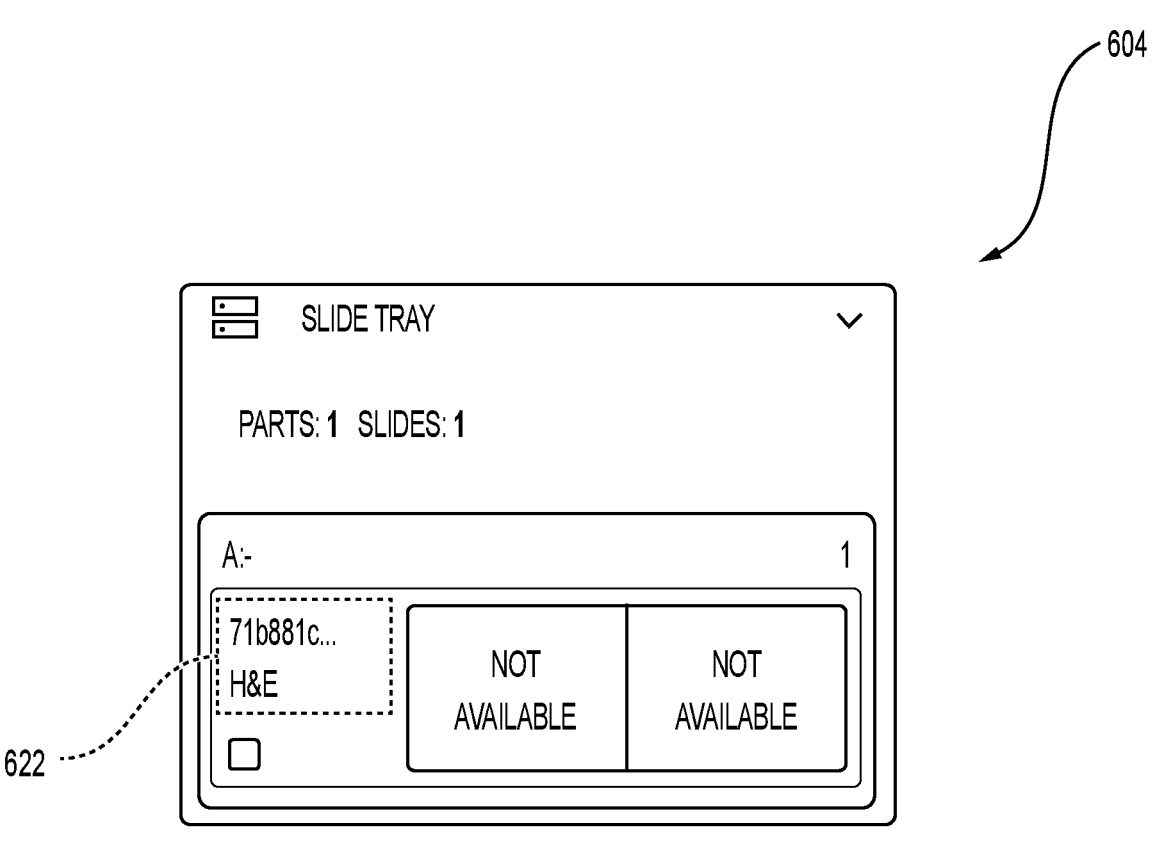
FIG. 6F is a slide tray of the viewer indicting a HER2-Low expression, according to an exemplary embodiment of the present disclosure.

FIG. 6E is a slide tray 604 of the viewer 600, according to an exemplary embodiment of the present disclosure. Patient and WSI information 620 may also be displayed in the slide tray 604. Further, the patient's name, MRN, date of birth, date of accession, number of parts and number of slides (i.e., WSIs) may be shown within the top part of the slide tray 604. Each slide in the slide tray 604 may be organized by part, and visible with a small preview (e.g., a thumbnail of the WSI). An indicator of the prediction output by the trained model may be included in each slide. For example, as shown in FIG. 6E, a red indicator 622 included on the top left of the slide indicates the trained model has identified a negative signal for HER2-expression (Null). Alternatively, if the trained model detects HER2-expression and the expression is identified as Low, the indicator 622 may be a different color (e.g., blue) as shown in FIG. 6F. While color is described herein, other visual schemes (e.g., animation, shading, highlighting, etc.) may be used to differentiate between the predictions output by the trained model. Users may be able to easily access a home screen via the home button 624, and a user menu via the user menu button 626. Lastly, the slide tray 604 may include an indicator 628 indicating the type of image analyzed by the viewer 600. The indicator 628 may allow for a user to access specific formatting preferences and/or user manuals.

In some examples, prior to providing the image as input to the trained model (e.g., the biomarker expression level tool 206), during the processing of the image by the trained model, and/or based on the output of the trained model, one or more different types of errors may be detected. In response to detecting an error, the system may generate a notification (e.g., a warning message or error message) to display to the user (e.g., through the viewer).

As one example, the system may be configured to process images having compatible file types, such as sys, isyntax, tiff, and/or ndpi file types, among other similar file types. If a file format is not compatible, the following warning may be returned: "Warning: file-type not supported." As another example, the system may be configured to accept WSIs that have been scanned using particular types of scanner (e.g., cleared scanners). The following warning messages generated and provided for display to users may have the following explanations as shown below in the chart.

| Warning Message to User | Explanation |
| --- | --- |
| Warning: device has not been validated with this slide file type | The file format used is supported but unvalidated. |
| Warning: slide file type is from an uncleared scanner | The file format used does not come from a cleared scanner. |

In other examples, the system may be configured to process digitized H&E breast biopsy and resection images. Therefore, if a WSI comprising a different type of tissue is identified, a notification may be generated alerting to the user that the WSI is unable to be processed by the system.

In further examples, if there are images for which the system device is unable to process for (a) technical reasons, or (b) an unsupported file format, and/or (c) abnormal amounts of tissues, the following errors displayed below in the table may be returned.

| Error Message to User | Cause of Error | Explanation |
| --- | --- | --- |
| Error: please contact support | File type error | The file extension of the uploaded file is not currently supported. |
| | File error | An error occurred while opening the specified slide. |
| | Slide abnormality error | The slide either contains no tissue, or contains tissue that is outside expected limits. |
| | Assertion Error | A runtime assertion occurred in the module. |
| | Runtime error | An error occurred while processing slide data or during model inference. |

FIG. 7 illustrates an exemplary flowchart for processing images to determine a biomarker expression level, according to techniques presented herein.

At step 702, one or more digital medical images may be received, the one or more digital medical images being of at least one pathology specimen associated with a patient.

At step 704, a biomarker expression level prediction for the one or more digital medical images may be determined by a machine learning system, the biomarker expression level prediction being based on a determined transcriptomic score and protein expression score for the one or more digital medical images.

Figure 8:
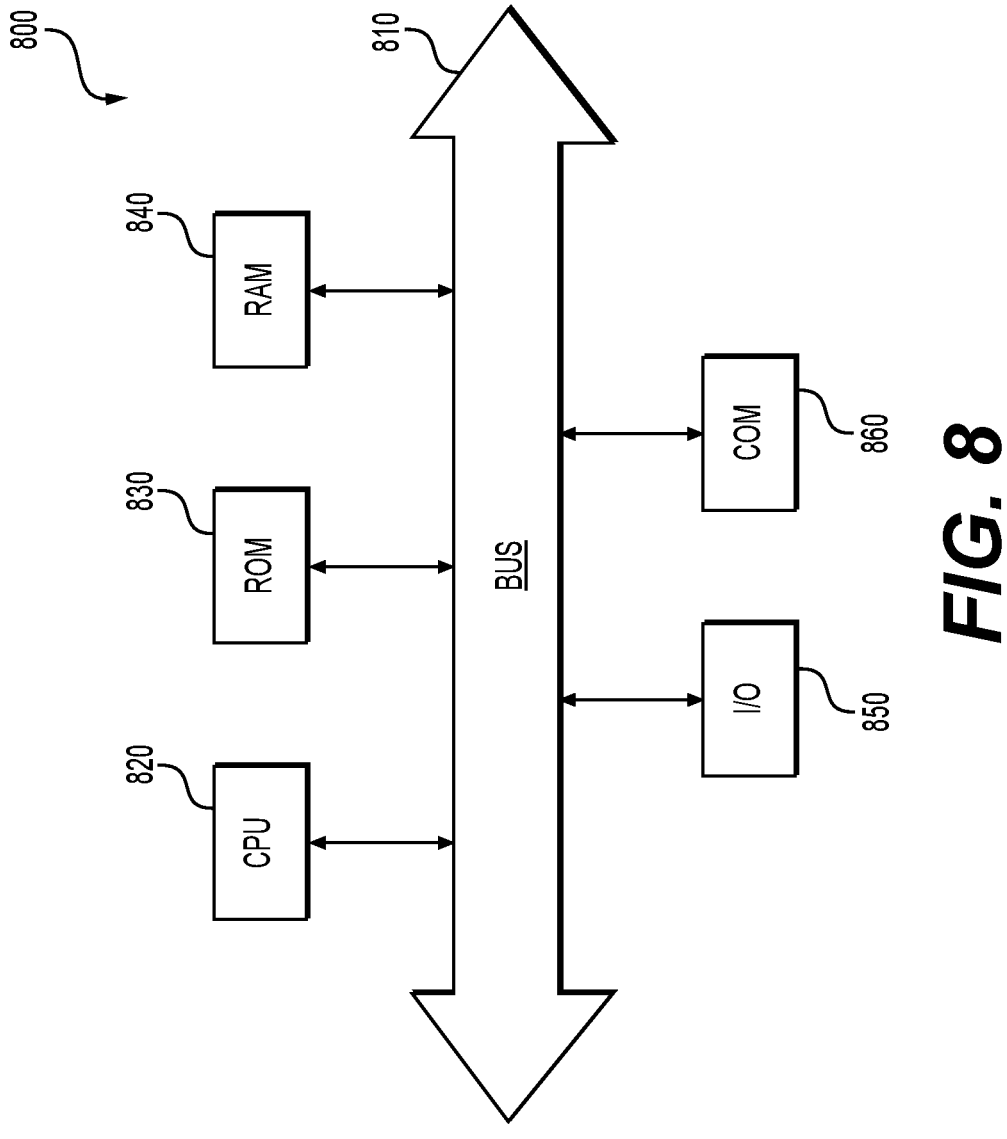
FIG. 8 depicts an example of a computing device that may execute techniques presented herein, according to one or more embodiments.

At step 706, a slide overlay may be generated, wherein the slide overlay indicates a region of tissue on the one or more digital medical images most likely to contribute to the slide level biomarker expression prediction As shown in FIG. 8, device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multi-processor system, such system operating alone, or in a cluster of computing devices operating in a cluster or server farm. CPU 820 may be connected to a data communication infrastructure 810, for example a bus, message queue, network, or multi-core message-passing scheme.

Device 800 may also include a main memory 840, for example, random access memory (RAM), and also may include a secondary memory 830. Secondary memory 830, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include similar means for allowing computer programs or other instructions to be loaded into device 800. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 800 may also include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for processing electronic medical images to predict a biomarker's presence, comprising:
   receiving one or more digital medical images, the one or more digital medical images being of at least one pathology specimen associated with a patient;
   determining a protein expression score for the one or more digital medical images, the protein expression score including an immunohistochemistry (IHC) score for each of the one or more digital medical images;
   determining a transcriptomic score including a level of Erb-B2 Receptor Tyrosine Kinase 2 (ERBB2) mRNA;
   determining, by a machine learning system, a biomarker expression level prediction for the one or more digital medical images, the biomarker expression level prediction being based on the transcriptomic score and the protein expression score for the one or more digital medical images, wherein the biomarker expression level prediction is determined to be a true absence of human epidermal growth factor receptor 2 (HER2) expression upon determining that the immunohistochemistry score is IHC-0+, indeterminate, or equivocal-IHC-1+ and that the ERBB2 mRNA level is less than a predetermined value; and
   generating a slide overlay indicating a region of tissue on the one or more digital medical images that contributes to the biomarker expression level prediction.

2. The method of claim 1, further comprising:
   determining, salient regions of the received one or more digital medical images prior to determining the biomarker expression level, wherein non-salient image regions are excluded from subsequent processing.

3. The method of claim 2, wherein the one or more salient regions correspond to cancerous tissue.

4. The method of claim 1, wherein the one or more digital medical images are images of breast tissue stained with hematoxylin and eosin.

5. The method of claim 1, wherein the biomarker expression is human epidermal growth factor receptor 2.

6. The method of claim 1, wherein the biomarker expression level prediction is performed upon determining that the received one or more slides has a immunohistochemistry (IHC) score of IHC-0 or IHC-1.

7. The method of claim 1, wherein the predetermined value of ERBB2 mRNA is 7.6.

8. The method of claim 1, wherein generating a slide overlay includes generating a tissue map overlay and/or a heatmap overlay.

9. A system for processing electronic medical images, the system comprising:
   at least one memory storing instructions; and
   at least one processor configured to execute the instructions to perform operations comprising:
      receiving one or more digital medical images, the one or more digital medical images being of at least one pathology specimen associated with a patient;
      determining a protein expression score for the one or more digital medical images, the protein expression score including an immunohistochemistry (IHC) score for each of the one or more digital medical images;
      determining a transcriptomic score including a level of Erb-B2 Receptor Tyrosine Kinase 2 (ERBB2) mRNA;
      determining, by a machine learning system, a biomarker expression level prediction for the one or more digital medical images, the biomarker expression level prediction being based on the transcriptomic score and the protein expression score for the one or more digital medical images, wherein the biomarker expression level prediction is determined to be a true absence of human epidermal growth factor receptor 2 (HER2) expression upon determining that the immunohistochemistry score is IHC-0+, indeterminate, or equivocal-IHC-1+ and that the ERBB2 mRNA level is less than a predetermined value; and generating a slide overlay indicating a region of tissue on the one or more digital medical images that contributes to the biomarker expression level prediction.

10. The system of claim 9, further comprising:

determining, salient regions of the received one or more digital medical images prior to determining the biomarker expression level, wherein non-salient image regions are excluded from subsequent processing.

11. The system of claim 10, wherein the one or more salient regions correspond to cancerous tissue.

12. The system of claim 9, wherein the biomarker expression level prediction is performed upon determining that the received one or more slides has a immunohistochemistry (IHC) score of IHC-0 or IHC-1.

13. The system of claim 9, wherein the one or more digital medical images are images of breast tissue stained with hematoxylin and eosin.

14. The system of claim 9, wherein the predetermined value is predetermined value of ERBB2 mRNA is 7.6.

15. A non-transitory computer-readable medium storing instructions that, when executed by a processor, perform operations processing electronic medical images, the operations comprising:

receiving one or more digital medical images, the one or more digital medical images being of at least one pathology specimen associated with a patient;

determining a protein expression score for the one or more digital medical images, the protein expression score including an immunohistochemistry (IHC) score for each of the one or more digital medical images;

determining a transcriptomic including a level of Erb-B2 Receptor Tyrosine Kinase 2 (ERBB2) mRNA;

determining, by a machine learning system, a biomarker expression level prediction for the one or more digital medical images, the biomarker expression level prediction being based on the transcriptomic score and the protein expression score for the one or more digital medical images, wherein the biomarker expression level prediction is determined to be a true absence of human epidermal growth factor receptor 2 (HER2) expression upon determining that the immunohistochemistry score is IHC-0+, indeterminate, or equivocal-IHC-1+ and that the ERBB2 mRNA level is less than a predetermined value; and generating a slide overlay indicating a region of tissue on the one or more digital medical images that contributes to the biomarker expression level prediction.

16. The non-transitory computer-readable medium of claim 15, further comprising:

determining, salient regions of the received one or more digital medical images prior to determining the biomarker expression level, wherein non-salient image regions are excluded from subsequent processing.

17. The non-transitory computer-readable medium of claim 16, wherein the one or more salient regions correspond to cancerous tissue.

18. The non-transitory computer-readable medium of claim 15, wherein the one or more digital medical images are images of breast tissue stained with hematoxylin and eosin.

19. The non-transitory computer-readable medium of claim 15, wherein the predetermined value of ERBB2 mRNA is 7.6.

* * * * *